(12) United States Patent
Kim et al.

(10) Patent No.: US 12,324,312 B2
(45) Date of Patent: Jun. 3, 2025

(54) DISPLAY DEVICE AND MANUFACTURING METHOD THEREOF

(71) Applicant: Samsung Display Co., Ltd., Yongin-si (KR)

(72) Inventors: Dae Hyun Kim, Yongin-si (KR); Veidhes Basrur, Yongin-si (KR); Xinxing Li, Yongin-si (KR); Tae Jin Kong, Yongin-si (KR); Hee Keun Lee, Yongin-si (KR); Hyun Min Cho, Yongin-si (KR); Keun Kyu Song, Yongin-si (KR); Jin Oh Kwag, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 622 days.

(21) Appl. No.: 17/277,832

(22) PCT Filed: Mar. 21, 2019

(86) PCT No.: PCT/KR2019/003331
§ 371 (c)(1),
(2) Date: Mar. 19, 2021

(87) PCT Pub. No.: WO2020/059990
PCT Pub. Date: Mar. 26, 2020

(65) Prior Publication Data
US 2022/0115470 A1 Apr. 14, 2022

(30) Foreign Application Priority Data
Sep. 21, 2018 (KR) .................. 10-2018-0114339

(51) Int. Cl.
*H10K 59/122* (2023.01)
*H01L 25/075* (2006.01)
(Continued)

(52) U.S. Cl.
CPC ....... *H10K 59/122* (2023.02); *H01L 25/0753* (2013.01); *H01L 25/167* (2013.01);
(Continued)

(58) Field of Classification Search
CPC ............... H10K 59/122; H10K 50/813; H10K 50/8426; H10K 59/124; H10K 59/126;
(Continued)

(56) References Cited

U.S. PATENT DOCUMENTS 9,112,112 B2 8/2015 Do et al.
9,263,704 B2 2/2016 Yoo et al.
(Continued)

FOREIGN PATENT DOCUMENTS

CN 104752482 A 7/2015
CN 108242217 A 7/2018
(Continued)

OTHER PUBLICATIONS

International Search Report dated Jul. 3, 2019 for PCT/KR2019/003331 (4 pages).

*Primary Examiner* — Britt D Hanley
*Assistant Examiner* — Victor V Barzykin
(74) *Attorney, Agent, or Firm* — Womble Bond Dickinson (US) LLP

(57) ABSTRACT

A display device may include: a base layer including a display area and a non-display area; and a plurality of pixels provided on the display area, and each including a plurality of sub-pixels. Each of the sub-pixels may include a pixel circuit layer, and a display element layer including an emission area formed to emit light, and a non-emission area provided around a perimeter of the emission area. The display element layer may include: a partition wall provided on the emission area of each of the sub-pixels; a bank provided on the non-emission area of each sub-pixel, and (Continued)

disposed on a surface equal to a surface on which the partition wall is disposed; a first electrode and a second electrode provided on the partition wall and spaced apart from each other; and at least one light emitting element provided between the first and second electrodes in the emission area of each sub-pixel, and configured to emit the light.

22 Claims, 19 Drawing Sheets

(51) Int. Cl.

| | | |
|---|---|---|
| *H01L 25/16* | (2023.01) | |
| *H10D 10/80* | (2025.01) | |
| *H10D 86/40* | (2025.01) | |
| *H10D 86/60* | (2025.01) | |
| *H10H 20/01* | (2025.01) | |
| *H10H 20/814* | (2025.01) | |
| *H10H 20/831* | (2025.01) | |
| *H10H 20/855* | (2025.01) | |
| *H10H 29/14* | (2025.01) | |
| *H10K 50/813* | (2023.01) | |
| *H10K 50/822* | (2023.01) | |
| *H10K 50/842* | (2023.01) | |
| *H10K 59/124* | (2023.01) | |
| *H10K 59/126* | (2023.01) | |
| *H10K 59/38* | (2023.01) | |
| *H10K 71/00* | (2023.01) | |
| *A01N 1/146* | (2025.01) | |
| *A61K 40/42* | (2025.01) | |
| *G08G 5/21* | (2025.01) | |
| *H05K 5/10* | (2025.01) | |
| *H10D 30/01* | (2025.01) | |
| *H10D 30/67* | (2025.01) | |
| *H10D 84/85* | (2025.01) | |
| *H10F 77/00* | (2025.01) | |
| *H10H 20/812* | (2025.01) | |
| *H10H 20/819* | (2025.01) | |
| *H10H 20/851* | (2025.01) | |
| *H10H 20/857* | (2025.01) | |
| *H10K 59/80* | (2023.01) | |

(52) U.S. Cl.
CPC ........... *H10D 10/821* (2025.01); *H10D 86/40* (2025.01); *H10D 86/60* (2025.01); *H10H 20/01* (2025.01); *H10H 20/8142* (2025.01); *H10H 20/831* (2025.01); *H10H 20/855* (2025.01); *H10H 29/142* (2025.01); *H10K 50/813* (2023.02); *H10K 50/822* (2023.02); *H10K 50/8426* (2023.02); *H10K 59/124* (2023.02); *H10K 59/126* (2023.02); *H10K 59/38* (2023.02); *H10K 71/00* (2023.02); *A01N 1/146* (2025.01); *A61K 40/4272* (2025.01); *G08G 5/21* (2025.01); *H05K 5/10* (2025.01); *H10D 30/0295* (2025.01); *H10D 30/6723* (2025.01); *H10D 84/858* (2025.01); *H10F 77/937* (2025.01); *H10H 20/812* (2025.01); *H10H 20/819* (2025.01); *H10H 20/8513* (2025.01); *H10H 20/857* (2025.01); *H10K 59/80515* (2023.02); *H10K 59/80521* (2023.02); *H10K 59/8722* (2023.02)

(58) Field of Classification Search
CPC ... H10K 59/38; H01L 25/0753; H01L 25/167; H01L 27/1214; H01L 27/156; H01L 33/58; H10D 10/821; H10H 20/8142
See application file for complete search history.

(56) References Cited

U.S. PATENT DOCUMENTS

| | | | |
|---|---|---|---|
| 9,570,425 | B2 | 2/2017 | Do |
| 9,773,761 | B2 | 9/2017 | Do |
| 10,249,603 | B2 | 4/2019 | Cho et al. |
| 10,340,419 | B2 | 7/2019 | Kim et al. |
| 10,367,123 | B2 | 7/2019 | Im et al. |
| 10,461,123 | B2 | 10/2019 | Kim et al. |
| 10,497,680 | B2 | 12/2019 | Sung et al. |
| 10,672,946 | B2 | 6/2020 | Cho et al. |
| 10,720,606 | B2 | 7/2020 | Song et al. |
| 2014/0141558 | A1* | 5/2014 | Osako ............... H10K 59/35 |
| | | | 438/35 |
| 2017/0358503 | A1 | 12/2017 | Liu et al. |
| 2018/0012876 | A1 | 1/2018 | Kim et al. |
| 2018/0012949 | A1 | 1/2018 | Takeya et al. |
| 2018/0175009 | A1* | 6/2018 | Kim .................. H01L 25/0753 |
| 2018/0240937 | A1 | 8/2018 | Park et al. |
| 2019/0019930 | A1 | 1/2019 | Do et al. |

FOREIGN PATENT DOCUMENTS

| | | | |
|---|---|---|---|
| EP | 3836217 | A1 | 6/2021 |
| EP | 3848969 | A1 | 7/2021 |
| KR | 10-1244926 | B1 | 3/2013 |
| KR | 10-1436123 | B1 | 11/2014 |
| KR | 10-1490758 | B1 | 2/2015 |
| KR | 10-2016-0092826 | A | 8/2016 |
| KR | 10-1711187 | B1 | 3/2017 |
| KR | 10-1730977 | B1 | 4/2017 |
| KR | 10-2018-0007025 | A | 1/2018 |
| KR | 10-2018-0007376 | A | 1/2018 |
| KR | 10-2018-0009014 | A | 1/2018 |
| KR | 10-2018-0055021 | A | 5/2018 |
| KR | 10-2018-0072909 | A | 7/2018 |
| KR | 10-1874993 | B1 | 7/2018 |
| KR | 10-1987196 | B1 | 6/2019 |
| KR | 10-2020-0001656 | A | 1/2020 |
| KR | 10-2020-0006208 | A | 1/2020 |
| KR | 10-2020-0031743 | A | 3/2020 |

* cited by examiner

DISPLAY DEVICE AND MANUFACTURING METHOD THEREOF

CROSS-REFERENCE TO RELATED APPLICATIONS

This application is a U.S. National Phase Patent Application of International Application Number PCT/KR2019/003331, filed on Mar. 21, 2019, which claims priority to Korean Patent Application No. 10-2018-0114339, filed on Sep. 21, 2018 in the Korean Intellectual Property Office, the entire content of all of which is incorporated herein by reference.

TECHNICAL FIELD

Various embodiments of the present disclosure relate to a display device, and more particularly, to a display device including a subminiature light emitting element and a method of manufacturing the display device.

BACKGROUND ART

A light emitting diode may have relatively satisfactory durability even under poor environmental conditions, and have excellent performances in terms of lifetime and luminance. Recently, research on the technology of applying such light emitting diodes to various display devices has become appreciably more active.

As a part of such research, technologies of fabricating a light emitting diode having a subminiature size corresponding to the micro-scale or the nano-scale using an inorganic crystalline structure, e.g., a structure obtained by growing a nitride-based semiconductor are being developed.

Light emitting diodes may be fabricated in a small size enough to form a pixel of a display device, etc. Light emitting diodes may be separately independently grown on a substrate, and the grown light emitting diodes may be separated therefrom and used to manufacture a display panel. In the case where a light emitting diode is used as a light source of the display panel, a plurality of light emitting diodes may be disposed in each pixel of the display panel. Here, if the plurality of light emitting diodes are disposed in close contact with each other, an undesired short-circuit may be caused between adjacent light emitting diodes, whereby the light emitting diodes may be damaged. As a result, a defect of a light emitting diode may occur.

DISCLOSURE

Technical Problem

Various embodiments of the present disclosure are directed to a display device formed through a simple manufacturing process with a reduced number of masks, and a method of manufacturing the display device.

Technical Solution

A display device in accordance with an embodiment of the present disclosure may include: a base layer comprising a display area and a non-display area; and a plurality of pixels provided in the display area, and each pixel of the plurality of pixels comprising a plurality of sub-pixels. Each sub-pixel of the sub-pixels may include a pixel circuit layer, and a display element layer, the display element layer comprising an emission area to emit light, and a non-emission area provided around a perimeter of the emission area. The display element layer may include: a partition wall provided in the emission area of each sub-pixel; a bank provided in the non-emission area of each sub-pixel, the bank being on the same surface as the partition wall is disposed; a first electrode and a second electrode provided on the partition wall and spaced apart from each other; and at least one light emitting element to emit the light, the light emitting element being between the first and the second electrodes in the emission area of each sub-pixel.

In an embodiment of the present disclosure, the partition wall and the bank may comprise an identical material and may be integral with each other.

In an embodiment of the present disclosure, the light emitting element comprises a first end and a second end opposite the first end. The display element layer may further include: a first contact electrode to electrically connect the first electrode with one of the first end or the second end of the light emitting element; and a second contact electrode to electrically connect the second electrode with a remaining one of the first end or the second end the light emitting element.

In an embodiment of the present disclosure, the display element layer may further include: a first insulating layer between the light emitting element and the pixel circuit layer; and a second insulating layer on a portion of an upper surface of the light emitting element.

In an embodiment of the present disclosure, the first contact electrode and the second contact electrode may be on an identical layer, and be spaced apart from each other on the second insulating layer and electrically insulated from each other.

In an embodiment of the present disclosure, the pixel circuit layer may include: at least one transistor on the base layer; and a passivation layer on the at least one transistor.

In an embodiment of the present disclosure, the passivation layer may be on the same surface as the partition wall and the bank.

In an embodiment of the present disclosure, the passivation layer may be integral with the partition wall and the bank, and may comprise a material identical with the identical material of the partition wall and the bank.

In an embodiment of the present disclosure, the display device may further include a conductive pattern between the base layer and the at least one transistor.

In an embodiment of the present disclosure, the conductive pattern may include a light shielding pattern to block light from entering a rear surface of the base layer.

In an embodiment of the present disclosure, the display device may further include: a color conversion layer on the display element layer, the color conversion layer comprising color conversion particles for converting the light to light having a set color; and a substrate on the color conversion layer.

In an embodiment of the present disclosure, the display device may further include: a substrate on the display element layer; and an intermediate layer between the display element layer and the substrate.

In an embodiment of the present disclosure, the intermediate layer may comprise an adhesive material for bonding the display element layer to the substrate.

In an embodiment of the present disclosure, the first electrode and the second electrode may be electrically separated from each other, and one of the first and the second electrodes may enclose a remaining one of the first electrode or the second electrode.

In an embodiment of the present disclosure, the light emitting element may include a subminiature light emitting diode in a shape of a cylinder or a polyprism, the subminiature light emitting diode being of a micro-scale or nano-scale size.

A method of manufacturing a display device in accordance with an embodiment of the present disclosure may include: providing a base layer comprising a plurality of sub-pixels, each sub-pixel of the plurality of sub-pixels comprising an emission area and a non-emission area; and forming, on the base layer, a display element layer to emit light from the emission area of each sub-pixel. The forming the display element layer may include: forming a partition wall in the emission area of each sub-pixel, and simultaneously forming a bank in the non-emission area of each sub-pixel; forming a first electrode and a second electrode spaced apart from each other on the partition wall; forming a first insulating layer to expose a portion of an upper surface of each of the first and the second electrodes; aligning a plurality of light emitting elements between the first and the second electrodes by respectively applying corresponding alignment voltages to the first and the second electrodes; forming, on the light emitting elements, a second insulating layer to expose opposite ends of each of the plurality of light emitting elements; and forming a first contact electrode and a second contact electrode on the second insulating layer.

In an embodiment of the present disclosure, the first contact electrode and the second contact electrode may be on an identical layer, be spaced apart from each other on the second insulating layer, and are electrically insulated from each other.

In an embodiment of the present disclosure, the forming the base layer may include: forming at least one transistor on the base layer; and forming a passivation layer on the at least one transistor. The passivation layer may be integral with the partition wall and the bank, and the passivation layer, the partition wall, and the bank comprise an identical material.

In an embodiment of the present disclosure, the first electrode and the second electrode may be electrically separated from each other, and one of the first and the second electrodes may enclose a remaining one of the first electrode or the second electrode.

Advantageous Effects

Various embodiments of the present disclosure may provide a display device formed through a comparatively simple manufacturing process with a reduced number of masks, and a method of manufacturing the display device.

The effects of the present disclosure are not limited by the foregoing, and other various effects are anticipated herein.

MODE FOR INVENTION

Figure 1A:
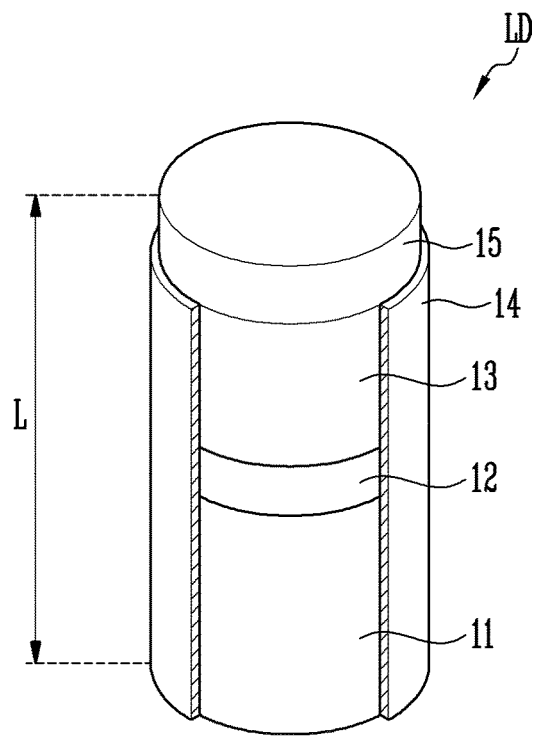
FIGS. 1A and 1B are perspective diagrams schematically illustrating a light emitting element in accordance with an embodiment of the present disclosure.

As the present disclosure allows for various changes and numerous embodiments, particular embodiments will be illustrated in the drawings and described in detail in the written description. However, this is not intended to limit the present disclosure to particular modes of practice, and it is to be appreciated that all changes, equivalents, and substitutes that do not depart from the spirit and technical scope of the present disclosure are encompassed in the present disclosure.

Throughout the disclosure, like reference numerals refer to like parts throughout the various figures and embodiments of the present disclosure. The sizes of elements in the accompanying drawings may be exaggerated for clarity of illustration. It will be understood that, although the terms "first", "second", etc. may be used herein to describe various elements, these elements should not be limited by these terms. These terms are only used to distinguish one element from another element. For instance, a first element discussed below could be termed a second element without departing from the teachings of the present disclosure. Similarly, the second element could also be termed the first element. In the present disclosure, the singular forms are intended to include the plural forms as well, unless the context clearly indicates otherwise.

It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof. Furthermore, when a first part such as a layer, a film, a region, or a plate is disposed on a second part, the first part may be not only directly on the second part but a third part may intervene between them. In addition, when it is expressed that a first part such as a layer, a film, a region, or a plate is formed on a second part, the surface of the second part on which the first part is formed is not limited to an upper surface of the second part but may include other surfaces such as a side surface or a lower surface of the second part. Similarly, when a first part, such as a layer, a film, a region, or a plate is under a second part, the first part may be not only directly under the second part, but a third part may intervene between them.

Embodiments and required details of the present disclosure are described with reference to the accompanying drawings in order to describe the present disclosure in detail so that those having ordinary knowledge in the technical field to which the present disclosure pertains can easily practice the present disclosure. Furthermore, a certain part may be multiple as long as it is not specifically mentioned in a sentence as one or single part.

Figure 1B:
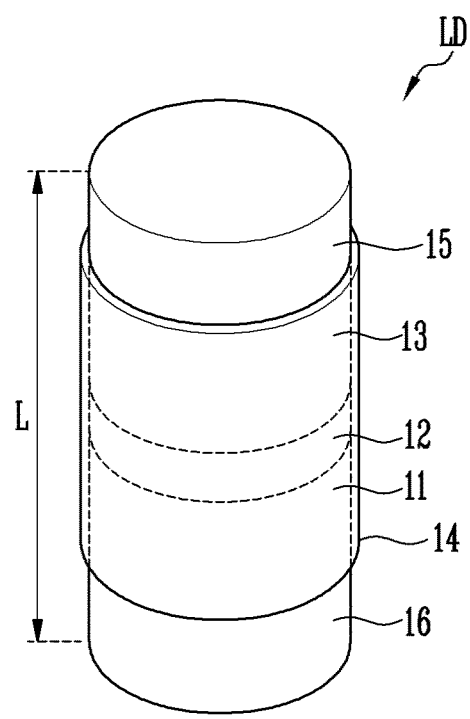

FIGS. 1A and 1B are perspective diagrams schematically illustrating a light emitting element in accordance with an embodiment of the present disclosure. Although FIGS. 1A and 1B illustrate cylindrical light emitting elements, the present disclosure is not limited thereto.

Referring to FIGS. 1A and 1B, a light emitting element LD in accordance with an embodiment of the present disclosure may include a first conductive semiconductor layer 11, a second conductive semiconductor layer 13, and an active layer 12 interposed between the first and second conductive semiconductor layers 11 and 13. For example, the light emitting element LD may be implemented as a stacked body formed by successively stacking the first conductive semiconductor layer 11, the active layer 12, and the second conductive semiconductor layer 13.

In an embodiment of the present disclosure, the light emitting element LD may be formed in a rod-like shape extending in one direction. If the direction in which the light emitting element LD extends is defined as a longitudinal direction, the light emitting element LD may have a first end and a second end in the extension direction. One of the first and second conductive semiconductor layers 11 and 13 may be disposed on the first end, and the other of the first and second conductive semiconductor layers 11 and 13 may be disposed on the second end.

Although the light emitting element LD may be provided in the form of a cylinder, the present disclosure is not limited thereto. The light emitting element LD may include a rod-like shape or a bar-like shape extending in the longitudinal direction (i.e., to have an aspect ratio greater than 1). For example, a length L of the light emitting element LD with respect to a longitudinal direction may be greater than the diameter thereof. The light emitting element LD may include a light emitting diode fabricated in a subminiature size having a diameter and/or length corresponding to, e.g., a micro-scale or nano-scale size.

However, the size of the light emitting element LD is not limited to this, and the size of the light emitting element LD may be changed to meet the requirements of a lighting device, or a self-emissive display device to which the light emitting element LD is applied.

The first conductive semiconductor layer 11 may include, for example, at least one n-type semiconductor layer. For instance, the first conductive semiconductor layer 11 may include a semiconductor layer which includes any one semiconductor material of InAlGaN, GaN, AlGaN, InGaN, AlN, and InN, and is doped with a first conductive dopant such as Si, Ge, or Sn. The material forming the first conductive semiconductor layer 11 is not limited to this, and the first conductive semiconductor layer 11 may be formed of various other materials.

The active layer 12 may be formed on the first conductive semiconductor layer 11 and have a single or multiple quantum well structure. In an embodiment of the present disclosure, a cladding layer (not illustrated) doped with a conductive dopant may be formed on and/or under the active layer 12. For example, the cladding layer may be formed of an AlGaN layer or an InAlGaN layer. In addition, material such as AlGaN or AlInGaN may be employed to form the active layer 12.

If an electric field having a predetermined voltage or more is applied to the opposite ends of the light emitting element LD, the light emitting element LD emits light by coupling of electron-hole pairs in the active layer 12.

The second conductive semiconductor layer 13 may be provided on the active layer 12 and may include a semiconductor layer of a type different from that of the first conductive semiconductor layer 11. For example, the second conductive semiconductor layer 13 may include at least one p-type semiconductor layer. For instance, the second conductive semiconductor layer 13 may include a semiconductor layer which includes any one semiconductor material of InAlGaN, GaN, AlGaN, InGaN, AlN, and InN, and is doped with a second conductive dopant such as Mg. The material forming the second conductive semiconductor layer 13 is not limited to this, and the second conductive semiconductor layer 13 may be formed of various other materials.

In an embodiment of the present disclosure, the light emitting element LD may further include one electrode layer 15 disposed on the second conductive semiconductor layer 13, as illustrated in FIG. 1A, as well as including the first conductive semiconductor layer 11, the active layer 12, and the second conductive semiconductor layer 13. Furthermore, in an embodiment, as shown in FIG. 1B, the light emitting element LD may further include another electrode layer 16 disposed on one end of the first conductive semiconductor layer 11, as well as including the electrode layer 15.

Although each of the electrode layers 15 and 16 may be formed of an ohmic contact electrode, the present disclosure is not limited thereto. Furthermore, the electrode layers 15 and 16 may include metal or a metal oxide. For example, chromium (Cr), titanium (Ti), aluminum (Al), gold (Au), nickel (Ni), ITO, and an oxide or alloy thereof may be used alone or in combination with each other. However, the present disclosure is not limited to this.

Materials included in the respective electrode layers 15 and 16 may be equal to or different from each other. The electrode layers 15 and 16 may be substantially transparent or semitransparent. Therefore, light generated from the light emitting element LD may pass through the electrode layers 15 and 16 and then be emitted outside the light emitting element LD.

In an embodiment of the present disclosure, the light emitting element LD may further include an insulating film 14. However, in some embodiments of the present disclosure, the insulating film 14 may be omitted, or may be provided to cover only some of the first conductive semiconductor layer 11, the active layer 12, and the second conductive semiconductor layer 13.

As illustrated in FIG. 1A, the insulating film 14 may be provided on a portion of the light emitting element LD other than one of opposite ends of the light emitting element LD. In this case, the insulating film 14 may expose only the one electrode layer 15 disposed on one end of the second conductive semiconductor layer 13 of the light emitting element LD and enclose the overall side surfaces of the components other than the electrode layer 15. Here, the insulating film 14 may allow at least the opposite ends of the light emitting element LD to be exposed to the outside. For example, the insulating film 14 may allow not only the electrode layer 15 disposed on one end of the second conductive semiconductor layer 13 but also one end of the first conductive semiconductor layer 11 to be exposed to the outside.

In an embodiment, as illustrated in FIG. 1B, in the case where the electrode layers 15 and 16 are disposed on the respective opposite ends of the light emitting element LD, the insulating film 14 may allow at least a portion of each of the electrode layers 15 and 16 to be exposed to the outside. Alternatively, in an embodiment, the insulating film 14 may not be provided.

In an embodiment of the present disclosure, the insulating film 14 may include transparent insulating material. For example, the insulating film 14 may include at least one insulating material selected from the group consisting of $SiO_2$, $Si_3N_4$, $Al_2O_3$, and $TiO_2$, but it is not limited thereto. In other words, various materials having insulating properties may be employed.

If the insulating film 14 is provided on the light emitting element LD, the active layer 12 may be prevented from short-circuiting with a first electrode and/or a second electrode, which is not illustrated. Thanks to the insulating film 14, occurrence of a defect on the surface of the light emitting element LD may be minimized, whereby the lifetime and efficiency of the light emitting element LD may be improved. In the case where a plurality of light emitting elements LD are disposed in close contact with each other, the insulating film 14 may prevent an undesired short-circuit from occurring between the light emitting elements LD.

The light emitting element LD may be employed as a light source for various display devices. The light emitting element LD may be fabricated through a surface treatment process.

Figure 2:
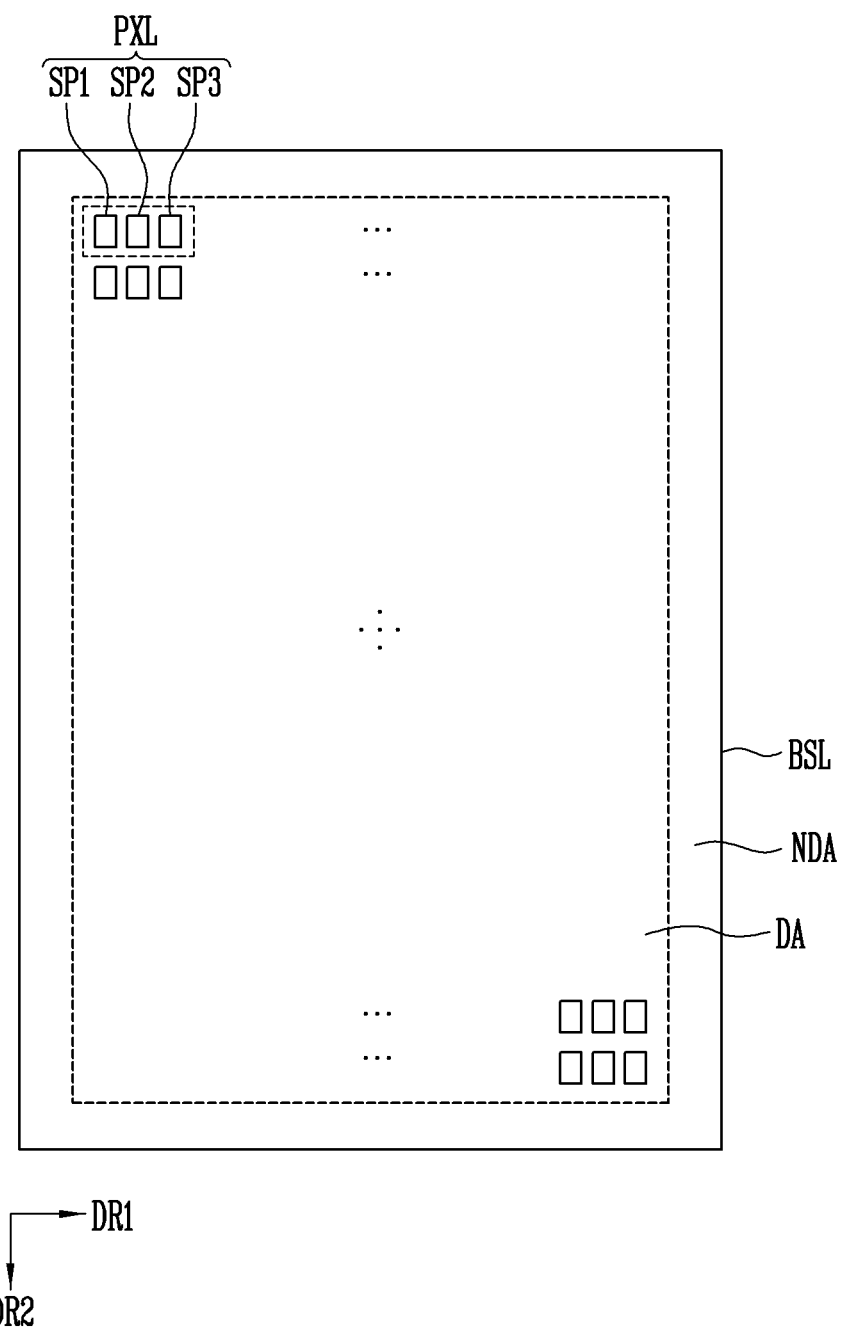
FIG. 2 illustrates a display device in accordance with an embodiment of the present disclosure, and particularly, is a schematic plan view illustrating a display device using the light emitting element illustrated in FIG. 1A as a light emitting source.

FIG. 2 illustrates a display device in accordance with an embodiment of the present disclosure, and particularly, is a schematic plan view illustrating a display device using the light emitting element illustrated in FIG. 1A as a light emitting source.

For the sake of explanation, FIG. 2 schematically illustrates the structure of the display device, focused on a display area in which an image is displayed. In some embodiments, although not illustrated, at least one driving circuit (e.g., a scan driver and a data driver) and/or a plurality of lines may be further provided in the display device.

Referring to FIGS. 1A and 2, the display device in accordance with the embodiment of the present disclosure may include a base layer BSL, pixels PXL provided on the base layer BSL and each including at least one light emitting element LD, a driver (not illustrated) provided on the base layer BSL and configured to drive the pixels PXL, and a line component (not illustrated) provided to connect the pixels PXL with the driver.

The display device may be classified into a passive-matrix type display device and an active-matrix type display device according to a driving method. For example, in the case where the display device in accordance with an embodiment is implemented as an active matrix type display device, each of the pixels PXL may include a driving transistor configured to control the amount of current to be supplied to the light emitting element LD, and a switching transistor configured to transmit data signals to the driving transistor.

Recently, active-matrix type display devices capable of selectively turning on each pixel PXL taking into account the resolution, the contrast, and the working speed have been mainstreamed. However, the present disclosure is not limited thereto. For example, passive-matrix type display devices in which pixels PXL may be turned on by groups may also employ components (e.g., first and second electrodes) for driving the light emitting element LD.

The base layer BSL may include a display area DA and a non-display area NDA.

In an embodiment, the display area DA may be disposed in a central portion of the display device, and the non-display area NDA may be disposed in a perimeter portion of the display device in such a way as to enclose the display area DA. The locations of the display area DA and the non-display area NDA are not limited to this, and the locations thereof may be changed.

The display area DA may be an area in which the pixels PXL for displaying an image are provided. The non-display area NDA may be an area in which the driver for driving the pixels PXL and some of the line unit for coupling the pixels PXL to the driver are provided.

The display area DA may have various shapes. For example, the display area DA may be provided in various forms such as a closed polygon including sides formed of linear lines, a circle, an ellipse or the like including a side formed of a curved line, and a semicircle, a semi-ellipse or the like including sides formed of a linear line and a curved line.

The non-display area NDA may be provided on at least one side of the display area DA. In an embodiment of the present disclosure, the non-display area NDA may enclose the display area DA.

The base layer BSL may be a rigid or flexible substrate, and the material or properties thereof are not particularly limited. For example, the base layer BSL may be a rigid substrate made of glass or reinforced glass, or a flexible substrate formed of a thin film made of plastic or metal. Furthermore, the base layer BSL may be a transparent substrate, but it is not limited thereto. For instance, the base layer BSL may be a translucent substrate, an opaque substrate, or a reflective substrate.

The pixels PXL may be disposed in the display area DA on the base layer BSL. Each of the pixels PXL refers to a smallest unit for displaying an image, and a plurality of pixels may be provided.

Each of the pixels PXL may include the light emitting element LD configured to be driven in response to a corresponding scan signal and a corresponding data signal. The light emitting element LD may have a small size corresponding to a nano-scale or a micro-scale, and be connected in parallel to light emitting elements disposed adjacent thereto. The light emitting element LD may form a light source of the corresponding pixel PXL.

Furthermore, each of the pixels PXL may include a plurality of sub-pixels. For example, each pixel PXL may include a first sub-pixel SP1, a second sub-pixel SP2, and a third sub-pixel SP3. In an embodiment, the first, second, and third sub-pixels SP1, SP2, and SP3 may emit light of different colors. For instance, the first sub-pixel SP1 may be a red sub-pixel for emitting red light, the second sub-pixel SP2 may be a green sub-pixel for emitting green light, and the third sub-pixel SP3 may be a blue sub-pixel for emitting blue light. However, the colors, types and/or number of sub-pixels forming each pixel PXL are not particularly limited. For example, the color of light which is emitted from each sub-pixel may be changed in various ways. Although in FIG. 2 there is illustrated an embodiment where the pixels PXL are arranged in the display area DA in a stripe shape, the present disclosure is not limited thereto. For instance, the display area DA may have various well-known pixel arrangement shapes.

The driver may provide a signal to each pixel PXL through the line component and thus control the operation of the pixel PXL. In FIG. 2, the line component is omitted for the convenience sake of explanation.

The driver may include a scan driver configured to provide scan signals to the pixels PXL through scan lines, an emission driver configured to provide emission control signals to the pixels PXL through emission control lines, a data driver configured to provide data signals to the pixels PXL through data lines, and a timing controller. The timing controller may control the scan driver, the emission driver, and the data driver.

FIGS. 3A to 3D are circuit diagrams illustrating examples of a unit light emitting area of the display device of FIG. 2 in accordance with various embodiments.

Referring to FIGS. 3A to 3D, each of the first to third sub-pixels may be configured of an active pixel. However, the type, the configuration, and/or the driving method of each of the first to third sub-pixels is not particularly limited. For example, each of the first to third sub-pixels may be configured of a pixel of a passive or active display device which can have various known structures.

Furthermore, referring to FIGS. 3A to 3D, the first to third sub-pixels may have substantially the same structure or similar structures. Hereinafter, for convenience sake, the first sub-pixel of the first to third sub-pixels will be described as a representative example.

Figure 3A:
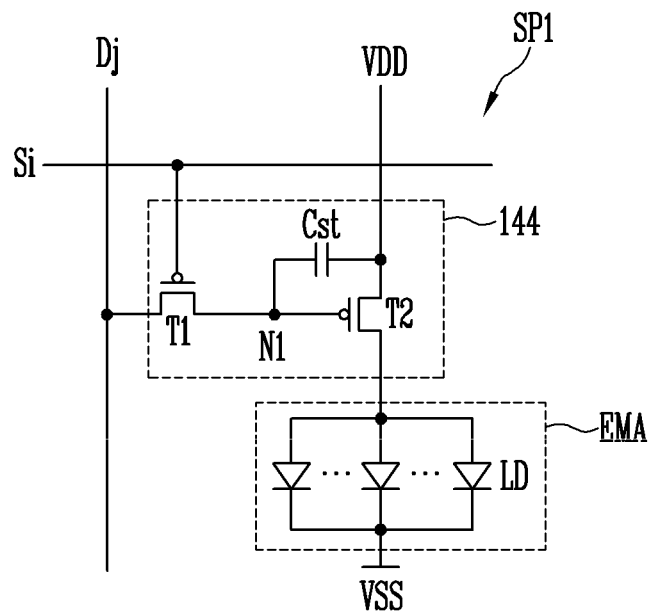
FIGS. 3A to 3D are circuit diagrams illustrating examples of a unit light emitting area of the display device of FIG. 2 in accordance with various embodiments.

Referring to FIGS. 1A, 2, and 3A, the first sub-pixel SP1 may include an emission circuit (or an emission area) EMA configured to generate light having a luminance corresponding to a data signal, and a pixel driving circuit 144 configured to drive the emission circuit EMA.

In an embodiment, the emission circuit EMA may include a plurality of light emitting elements LD connected parallel to each other between a first driving power supply VDD and a second driving power supply VSS (or referred as to second driving power). The first driving power supply VDD and the second driving power supply VSS may have different potentials. For example, the first driving power supply VDD may be set as a high-potential power supply, and the second driving power supply VSS may be set as a low-potential power supply. Here, a difference in potential between the first and second driving power supplies VDD and VSS may be set to a threshold voltage of the light emitting elements LD or more during an emission period of the first sub-pixel SP1. A first electrode (e.g., an anode electrode) of each of the light emitting elements LD may be electrically connected to the first driving power supply VDD via the pixel driving circuit 144. A second electrode (e.g., a cathode electrode) of each of the light emitting elements LD may be electrically connected to the second driving power supply VSS.

Each of the light emitting elements LD may emit light at a luminance corresponding to a driving current which is controlled by the pixel driving circuit 144.

Figure 3B:
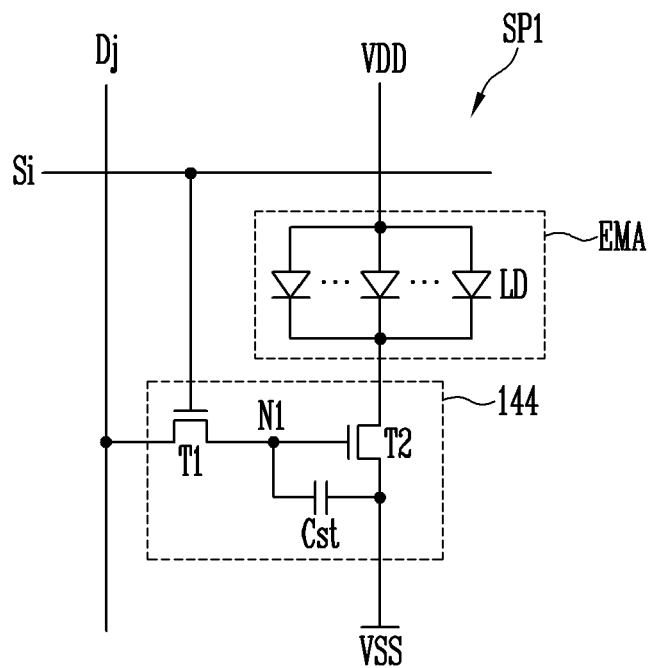
Figure 3C:
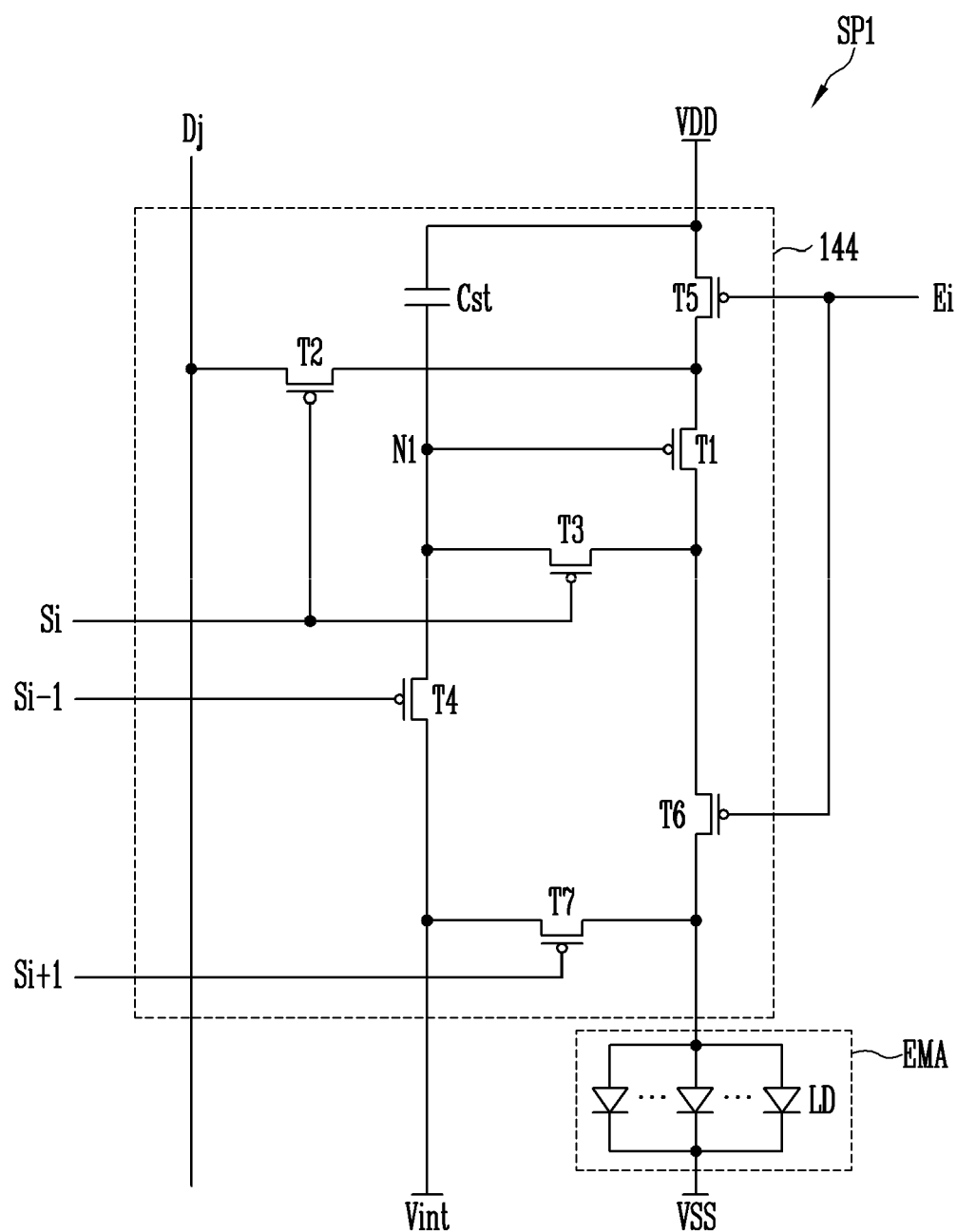

Although FIGS. 3A to 3C illustrate embodiments in which the light emitting elements LD are connected in parallel to each other in the same direction (e.g., a forward direction) between the first and second driving power supplies VDD and VSS, the present disclosure is not limited thereto. For example, in an embodiment, some of the light emitting elements LD may be connected to each other in the forward direction between the first and second power supplies VDD and VSS, and the other light emitting elements LD may be connected to each other in the reverse direction. One of the first and second driving power supplies VDD and VSS may be supplied in the form of an AC voltage. In this case, the light emitting elements LD connected in the forward direction and the light emitting elements LD connected in the reverse direction may alternately emit light. As another embodiment, in an embodiment, the first sub-pixel SP1 may include only a single light emitting element LD.

In an embodiment of the present disclosure, the pixel driving circuit 144 may include first and second transistors T1 and T2, and a storage capacitor Cst. The structure of the pixel driving circuit 144 is not limited to that of the embodiment illustrated in FIG. 3A.

A first electrode of the first transistor (switching transistor) T1 is electrically connected to a data line Dj, and a second electrode thereof is electrically connected to a first node N1. Here, the first electrode and the second electrode of the first transistor T1 may be different electrodes. For example, if the first electrode is a source electrode, the second electrode is a drain electrode. A gate electrode of the first transistor T1 is connected to the scan line Si.

When a scan signal having a voltage (e.g., a low-level voltage) capable of turning on the first transistor T1 is supplied from the scan line Si, the first transistor T1 is turned on to electrically connect the data line Dj with the first node N1. Here, a data signal of a corresponding frame is supplied to the data line Dj, whereby the data signal is transmitted to the first node N1. The data signal transmitted to the first node N1 may be charged into the storage capacitor Cst.

A first electrode of the second transistor (driving transistor) T2 is electrically connected to the first driving power supply VDD, and a second electrode thereof is electrically connected to the first electrode of each of the light emitting elements LD. A gate electrode of the second transistor T2 is electrically connected to the first node N1. As such, the second transistor T2 may control the amount of driving current to be supplied to the light emitting elements LD in response to the voltage of the first node N1.

One electrode of the storage capacitor Cst is electrically connected to the first driving power supply VDD, and the other electrode thereof is electrically connected to the first node N1. The storage capacitor Cst is charged with a voltage corresponding to a data signal supplied to the first node N1, and maintains the charged voltage until a data signal of a subsequent frame is supplied.

For the sake of explanation, FIG. 3A illustrates the pixel driving circuit 144 having a relatively simple structure including the first transistor T1 configured to transmit the data signal to the first sub-pixel SP1, the storage capacitor Cst configured to store the data signal, and the second transistor T2 configured to supply driving current corresponding to the data signal to the light emitting elements LD.

However, the present disclosure is not limited thereto, and the structure of the pixel driving circuit 144 may be changed in various ways. For example, the pixel driving circuit 144 may further include at least one transistor element such as a transistor element configured to compensate for the threshold voltage of the second transistor T2, a transistor element configured to initialize the first node N1, and/or a transistor element configured to control an emission time of the light emitting elements LD, or other circuit elements such as a boosting capacitor for boosting the voltage of the first node N1.

Furthermore, although in FIG. 3A the transistors, e.g., the first and second transistors T1 and T2, included in the pixel driving circuit 144 have been illustrated as being formed of P-type transistors, the present disclosure is not limited to this. In other words, at least one of the first and second transistors T1 and T2 included in the pixel driving circuit 144 may be changed to an N-type transistor.

Referring to FIGS. 1A, 2, and 3B, the first and second transistors T1 and T2 in accordance with an embodiment of the present disclosure may be formed of N-type transistors. The configuration and operation of the pixel driving circuit 144 illustrated in FIG. 3B, other than a change in connection positions of some components due to a change in the type of transistor, are similar to those of the pixel driving circuit 144 of FIG. 3A. Therefore, detailed descriptions pertaining to this will be omitted.

In an embodiment of the present disclosure, the configuration of the pixel driving circuit 144 is not limited to the embodiments illustrated in FIGS. 3A and 3B. For example, the pixel driving circuit 144 may be configured in the same manner as that of an embodiment illustrated in FIG. 3C.

Referring to FIGS. 1A, 2, and 3C, the pixel driving circuit 144 may be electrically connected to the scan line Si and the data line Dj of the first sub-pixel SP1. For example, if the first sub-pixel SP1 is disposed on an i-th row and a j-th column of the display area DA, the pixel driving circuit 144 of the first sub-pixel SP1 may be electrically connected to an i-th scan line Si and a j-th data line Dj of the display area DA.

In an embodiment, the pixel driving circuit 144 may also be electrically connected to at least one scan line. For example, the first sub-pixel SP1 disposed on the i-th row of the display area DA may be further electrically connected to an i−1-th scan line Si−1 and/or an i+1-th scan line Si+1.

In an embodiment, the pixel driving circuit 144 may be electrically connected not only to the first and second driving power supplies VDD and VSS but also to a third power supply. For example, the pixel driving circuit 144 may also be electrically connected to an initialization power supply Vint.

The pixel driving circuit 144 may include first to seventh transistors T1 to T7, and a storage capacitor Cst.

A first electrode of the first transistor (driving transistor) T1, e.g., a source electrode, may be electrically connected to the first driving power supply VDD via the fifth transistor T5, and a second electrode thereof, e.g., a drain electrode, may be connected to first end of light emitting elements LD via the sixth transistor T6. A gate electrode of the first transistor T1 may be connected to a first node N1. The first transistor T1 may control driving current flowing between the first driving power supply VDD and the second driving power supply VSS via the light emitting elements LD in response to the voltage of the first node N1.

The second transistor (switching transistor) T2 may be electrically connected between the j-th data line Dj electrically connected to the first sub-pixel SP1 and the source electrode of the first transistor T1. A gate electrode of the second transistor T2 is electrically connected to the i-th scan line Si electrically connected to the first sub-pixel SP1. When a scan signal having a gate-on voltage (e.g., a low-level voltage) is supplied from the i-th scan line Si, the second transistor T2 is turned on to electrically connect the j-th data line Dj to the source electrode of the first transistor T1. Hence, if the second transistor T2 is turned on, a data signal supplied from the j-th data line Dj may be transmitted to the first transistor T1.

The third transistor T3 is electrically connected between the drain electrode of the first transistor T1 and the first node N1. A gate electrode of the third transistor T3 is electrically connected to the i-th scan line Si. When a scan signal having a gate-on voltage is supplied from the scan line Si, the third transistor T3 is turned on to electrically connect the drain electrode of the first transistor T1 to the first node N1.

Therefore, when the third transistor T3 is turned on, the first transistor T1 may be connected in the form of a diode (or diode-connected).

The fourth transistor T4 may be electrically connected between the first node N1 and an initialization power supply Vint. A gate electrode of the fourth transistor T4 is electrically connected to a preceding scan line, e.g., an i−1-th scan line Si−1. When a scan signal of a gate-on voltage is supplied to the i−1-th scan line Si−1, the fourth transistor T4 is turned on so that the voltage of the initialization power supply Vint may be transmitted to the first node N1. Here, the initialization power supply Vint may have a voltage equal to or less than the minimum voltage of the data signal.

The fifth transistor T5 is electrically connected between the first driving power supply VDD and the first transistor T1. A gate electrode of the fifth transistor T5 is electrically connected to a corresponding emission control line, e.g., an i-th emission control line Ei. The fifth transistor T5 may be turned off when an emission control signal having a gate-off voltage is supplied to the i-th emission control line Ei, and may be turned on in other cases.

The sixth transistor T6 is electrically connected between the first transistor T1 and first ends of the light emitting elements LD. A gate electrode of the sixth transistor T6 may be electrically connected to the i-th emission control line Ei. The sixth transistor T6 may be turned off when an emission control signal having a gate-off voltage is supplied to the i-th emission control line Ei, and may be turned on in other cases.

The seventh transistor T7 is electrically connected between the first ends of the light emitting elements LD and the initialization power supply Vint. A gate electrode of the seventh transistor T7 is electrically connected to any one of scan lines of a subsequent stage, e.g., to the i+1-th scan line Si+1. When a scan signal of a gate-on voltage is supplied to the i+1-th scan line Si+1, the seventh transistor T7 may be turned on so that the voltage of the initialization power supply Vint may be supplied to the first ends of the light emitting elements LD.

The storage capacitor Cst is connected between the first driving power supply VDD and the first node N1. The storage capacitor Cst may store a voltage corresponding both to the data signal applied to the first node N1 during each frame period, and to the threshold voltage of the first transistor T1.

For convenience sake, FIG. 3C illustrates that all of the first to seventh transistors T1 to T7 are formed of P-type transistors, but the present disclosure is not limited thereto. For example, at least one of the first to seventh transistors T1 to T7 included in the pixel driving circuit 144 may be formed of an N-type transistor, or all of the first to seventh transistors T1 to T7 may be formed of N-type transistors.

Figure 3D:
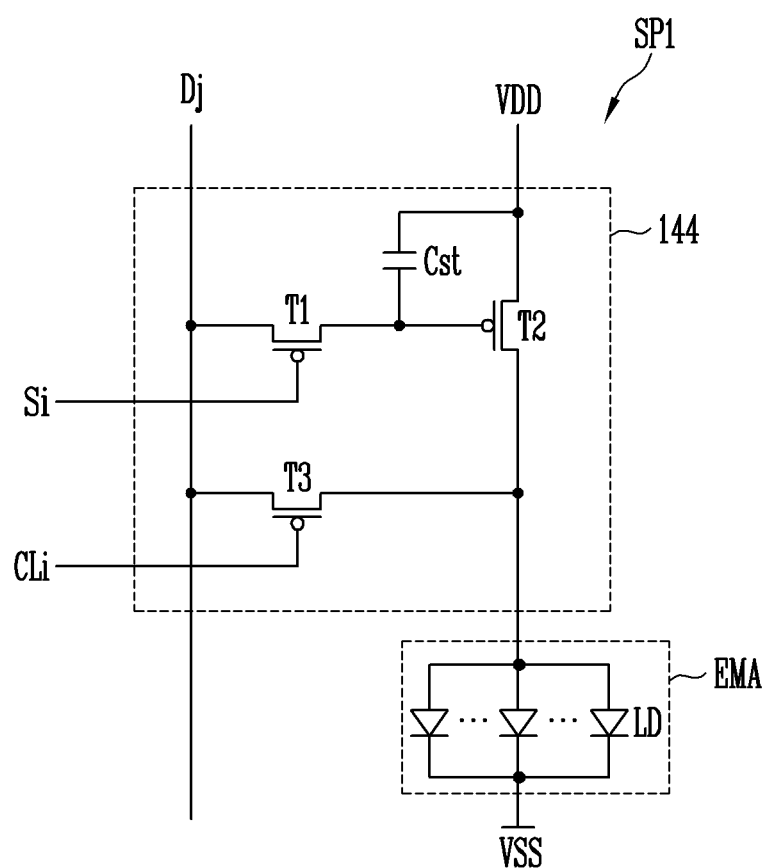

In an embodiment, as illustrated in FIG. 3D, the pixel driving circuit 144 may further include a third transistor T3 as well as including the first and second transistors T1 and T2. The third transistor T3 may be connected between the j-th data line Dj and the anode electrode of each of the light emitting elements LD. The gate electrode of the third transistor T3 may be connected to the control line CLi so that the third transistor T3 may be turned on when a control signal is supplied to the control line CLi, and be turned off in other cases.

For convenience sake, FIG. 3D illustrates that all of the first to third transistors T1 to T3 are formed of P-type transistors, but the present disclosure is not limited thereto. For example, at least one of the first to third transistors T1 to T3 included in the pixel driving circuit 144 may be formed of an N-type transistor, or all of the first to third transistors T1 to T3 may be formed of N-type transistors.

Figure 4:
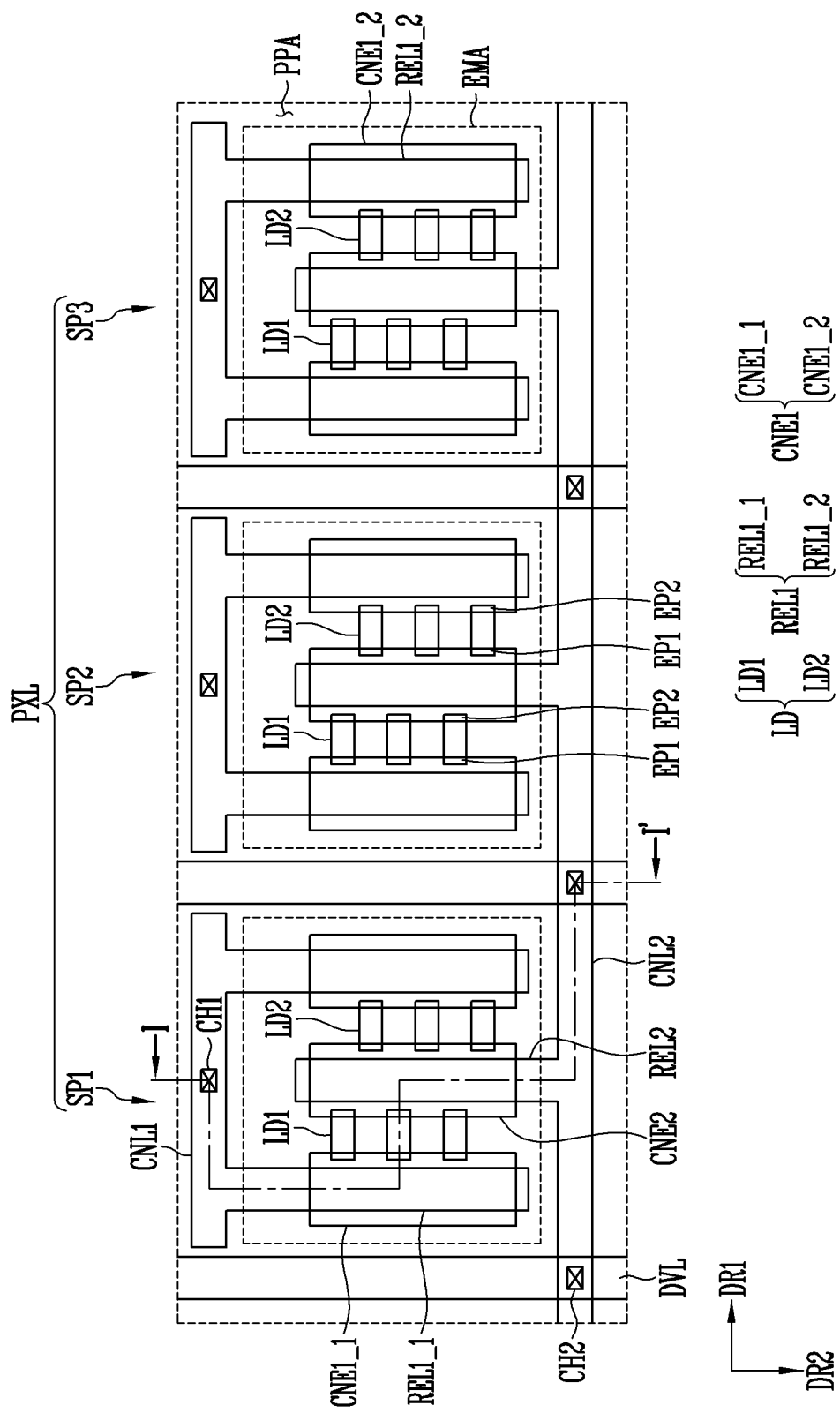
FIG. 4 is a plan view schematically illustrating first to third sub-pixels included in one of the pixels illustrated in FIG. 2.
Figure 5:
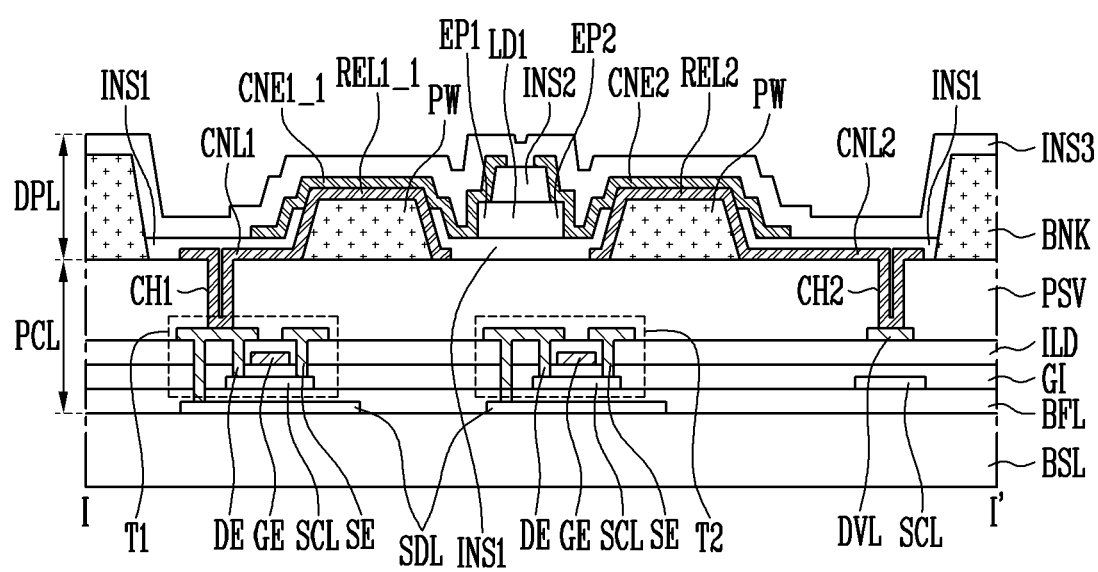
FIG. 5 is a sectional view taken along line I-I' of FIG. 4.

FIG. 4 is a plan view schematically illustrating first to third sub-pixels included in one of the pixels illustrated in FIG. 2, and FIG. 5 is a sectional view taken along line I-I' of FIG. 4.

In FIG. 4, for the sake of explanation, a plurality of light emitting elements provided in each sub-pixel are illustrated as being horizontally aligned. However, the alignment of the light emitting elements is not limited thereto. For example, at least some of the light emitting elements may be aligned in a direction intersecting with the horizontal direction.

Furthermore, for the sake of explanation, illustration of transistors connected to the light emitting elements, and signal lines connected to the transistors has been omitted in FIG. 4.

Moreover, although FIGS. 4 and 5 illustrate a simplified structure of the one pixel, e.g., showing that each electrode has only a single electrode layer, the present disclosure is not limited thereto.

Referring to FIGS. 1A to 5, the display device in accordance with an embodiment of the present disclosure may include a base layer BSL on which a plurality of pixels PXL are provided.

Each of the pixels PXL may include a first sub-pixel SP1, a second sub-pixel SP2, and a third sub-pixel SP3 which are provided on the base layer BSL. In an embodiment of the present disclosure, the first sub-pixel SP1 may be a red sub-pixel, the second sub-pixel SP2 may be a green sub-pixel, and the third sub-pixel SP3 may be a blue sub-pixel.

Each of the first to third sub-pixels SP1 to SP3 may include an emission area EMA which emits light, and a non-emission PPA disposed around a perimeter of the emission area EMA. In an embodiment of the present disclosure, a pixel area of each of the first to third sub-pixels SP1 to SP3 may include an emission area EMA and a non-emission area PPA of the corresponding sub-pixel.

A base layer BSL, a pixel circuit layer PCL, and a display element layer DPL may be provided in the pixel area of each of the first to third sub-pixel SP1 to SP3.

The pixel circuit layer PCL of each of the first to third sub-pixels SP1 to SP3 may include a buffer layer BFL disposed on the base layer BSL, first and second transistors T1 and T2 disposed on the buffer layer BFL, and a driving voltage line DVL. Furthermore, the pixel circuit layer PCL of each of the first to third sub-pixels SP1 to SP3 may further include a passivation layer PSV which is provided on the first and second transistors T1 and T2 and the driving voltage line DVL.

The base layer BSL may include insulating material such as glass, an organic polymer, or crystal. Furthermore, the base layer BSL may be made of material having flexibility so as to be bendable or foldable, and have a single-layer or multi-layer structure.

The buffer layer BFL may be provided on the base layer BSL and may prevent impurities from diffusing into the first and second transistors T1 and T2. The buffer layer BFL may be omitted depending on the material of the base layer BSL or processing conditions.

A light shielding pattern SDL may be provided between the base layer BSL and the buffer layer BFL.

The light shielding pattern SDL may be a light shielding layer which is formed of conductive material, insulating material, etc., and blocks light introduced into a rear surface of the base layer BSL so that the light can be blocked from being introduced into the pixel circuit layer PCL of each of the first to third sub-pixels SP1, SP2, and SP3. In an embodiment, the light shielding pattern SDL may include a black matrix. The light shielding pattern SDL may be provided on the base layer BSL to correspond to a lower portion of the semiconductor layer SCL of each of the first and second transistors T1 and T2. In an embodiment, the light shielding pattern SDL may be formed of a metal, which is conductive material. In this case, the light shielding pattern SDL may be electrically connected to a component of any one transistor of the first and second transistors T1 and T2.

The first transistor T1 may be a driving transistor, which is electrically connected to some of the light emitting elements LD provided in the display element layer DPL of a corresponding sub-pixel to drive the light emitting elements LD. The second transistor T2 may be a switching transistor configured to switch the first transistor T1.

Each of the first and second transistors T1 and T2 may include a semiconductor layer SCL, a gate electrode GE, and source and drain electrodes SE and DE.

The semiconductor layer SCL may be disposed on the buffer layer BFL. The semiconductor layer SCL may include a source area which comes into contact with the source electrode SE, and a drain area which comes into contact with the drain electrode DE. An area between the source area and the drain area may be a channel area.

The semiconductor layer SCL may be a semiconductor pattern formed of polysilicon, amorphous silicon, an oxide semiconductor, etc. The channel area may be an intrinsic semiconductor, which is an undoped semiconductor pattern. Each of the source area and the drain area may be a semiconductor pattern doped with an impurity.

The gate electrode GE may be provided on the semiconductor layer SCL with the gate insulating layer GI interposed therebetween.

The source electrode SE and the drain electrode DE may respectively come into contact with the source area and the drain area of the semiconductor layer SCL through corresponding contact holes which pass through an interlayer insulating layer ILD and the gate insulating layer GI.

In an embodiment of the present disclosure, each of the first and second transistors T1 and T2 included in the pixel circuit layer PCL provided in each sub-pixel may be formed of an LTPS thin-film transistor, but the present disclosure is not limited thereto. In some embodiments, each of the first and second transistors T1 and T2 may be formed of an oxide semiconductor thin-film transistor.

The drain electrode DE of each of the first and second transistors T1 and T2 may be electrically connected with the light shielding pattern SDL provided on the base layer BSL. In detail, the drain electrode DE of each of the first and second transistors T1 and T2 may be electrically connected to a corresponding light shielding pattern SDL through a contact hole successively passing through the interlayer insulating layer ILD, the gate insulating layer GI, and the buffer layer BFL.

The driving voltage line DVL may be provided on the interlayer insulating layer ILD, but the present disclosure is not limited thereto. In some embodiments, the driving voltage line DVL may be provided on any one of the insulating layers included in the pixel circuit layer PCL. The second driving power supply (VSS of FIG. 3A) may be applied to the driving voltage line DVL.

The passivation layer PSV may include a first contact hole CH1 which exposes a portion of the drain electrode DE of the first transistor T1, and a second contact hole CH2 which exposes a portion of the driving voltage line DVL.

The display element layer DPL of each of the first to third sub-pixels SP1 to SP3 may include a partition wall PW, first and second electrodes REL1 and REL2, first and second connection lines CNL1 and CNL2, a plurality of light emitting elements LD, and first and second contact electrodes CNE1 and CNE2 which are provided on the passivation layer PSV.

The partition wall PW may be provided on the passivation layer PSV in the emission area EMA of each of the first to third sub-pixels SP1 to SP3. A bank BNK formed of the same material as that of the partition wall PW may be formed and/or provided in the non-emission area PPA between adjacent sub-pixels to define the emission area EMA of each sub-pixel.

Figure 8A:
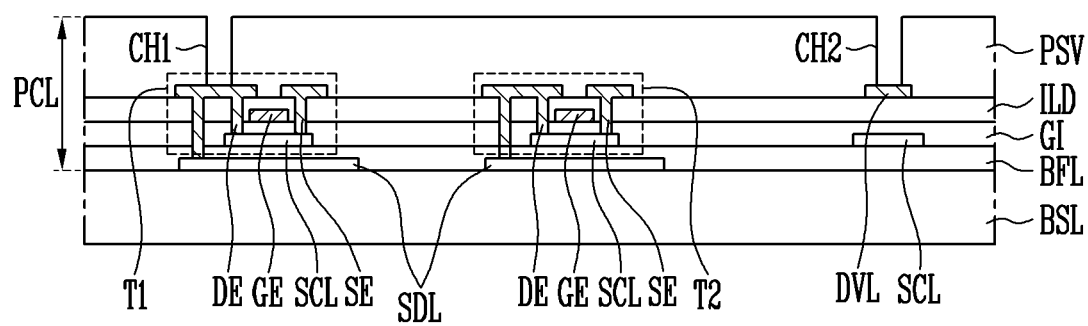
FIGS. 8A to 8H are sectional diagrams sequentially illustrating a method of manufacturing the display device of FIG. 5.
Figure 8B:
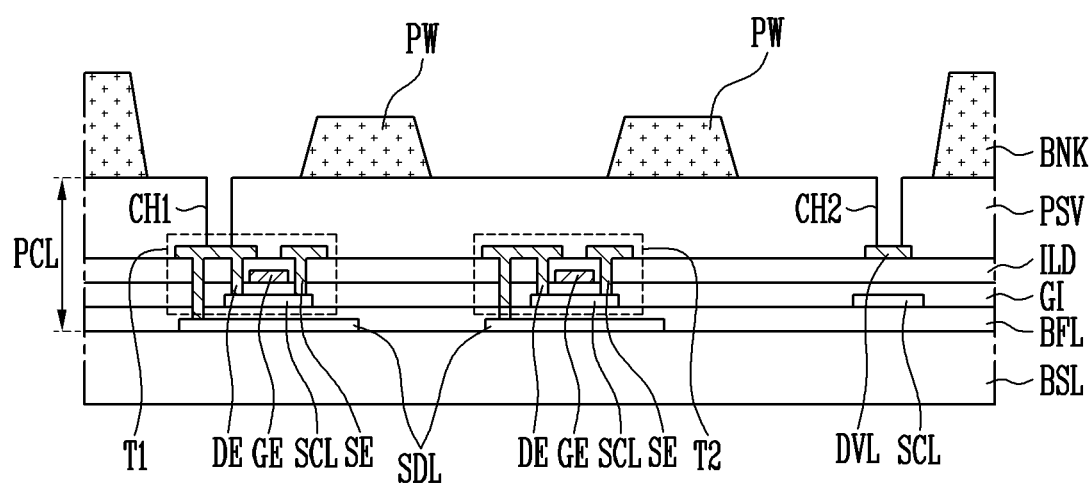
Figure 8C:
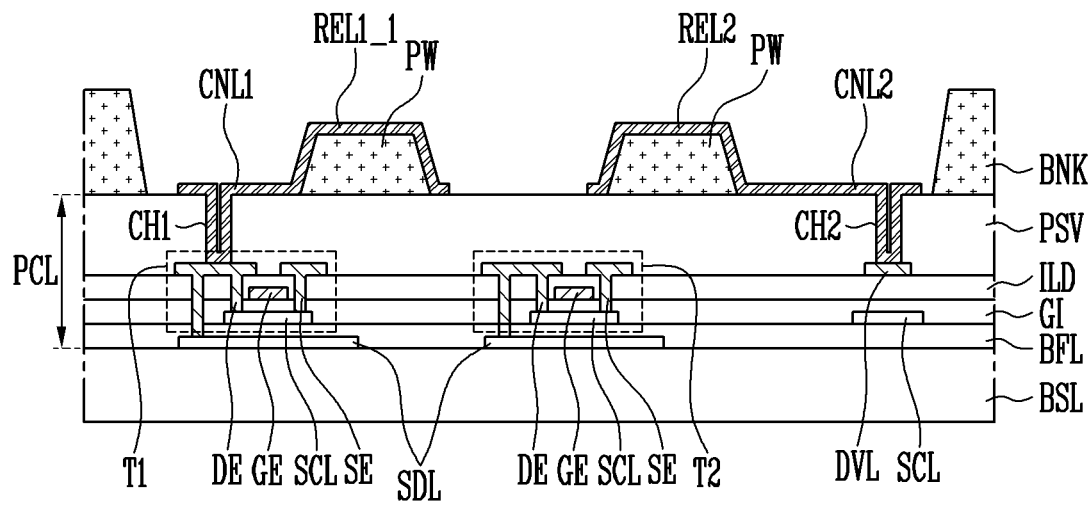
Figure 8D:
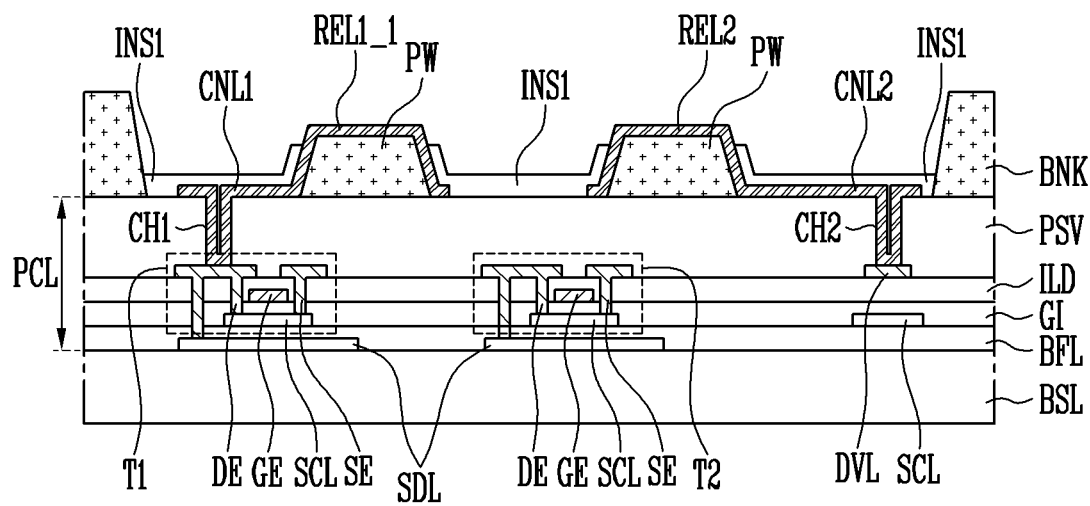
Figure 8E:
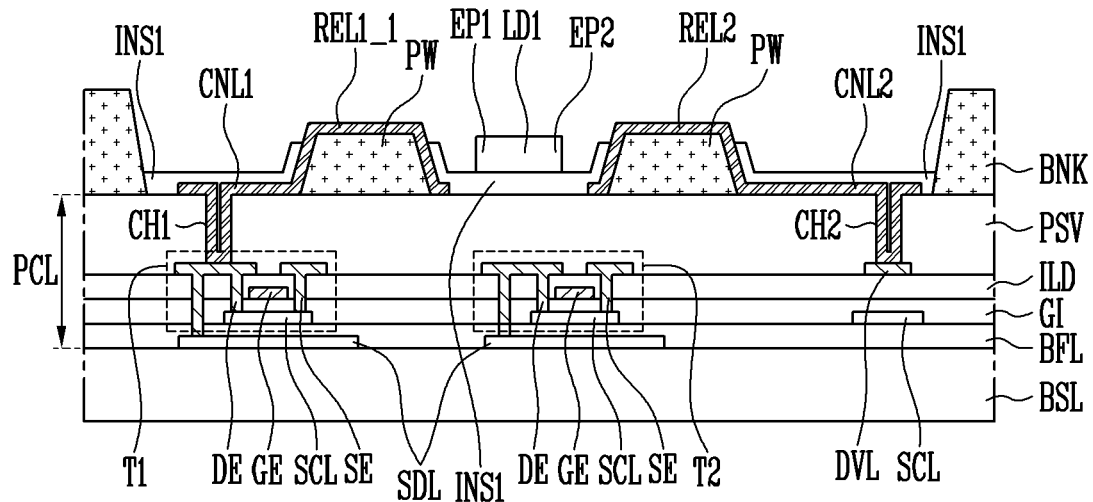
Figure 8F:
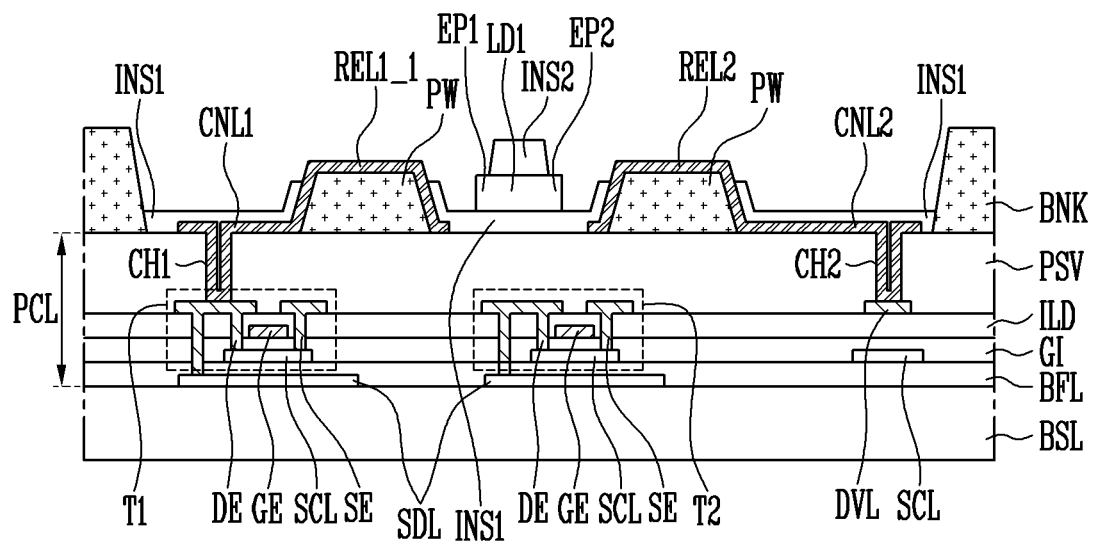
Figure 8G:
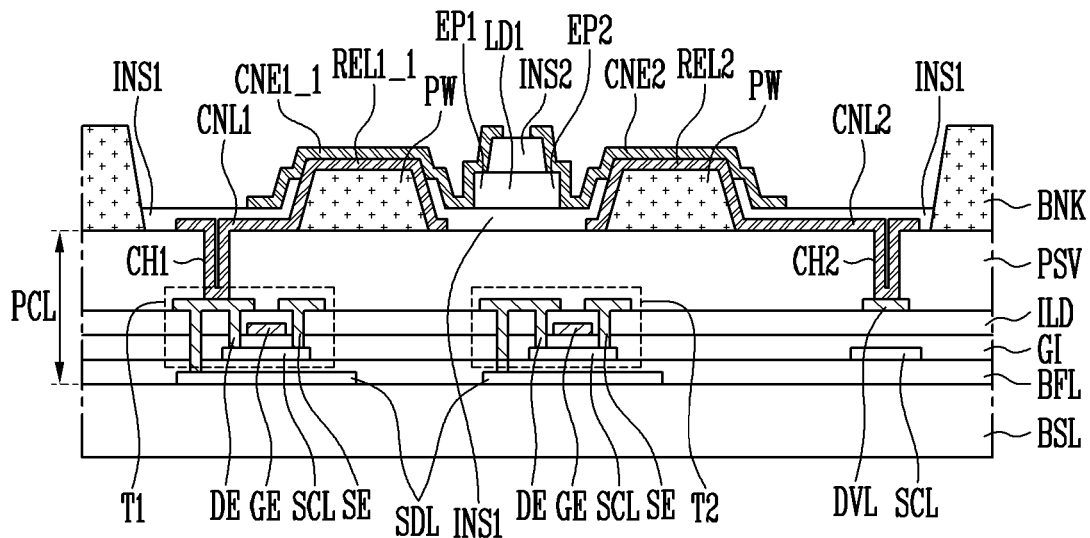
Figure 8H:
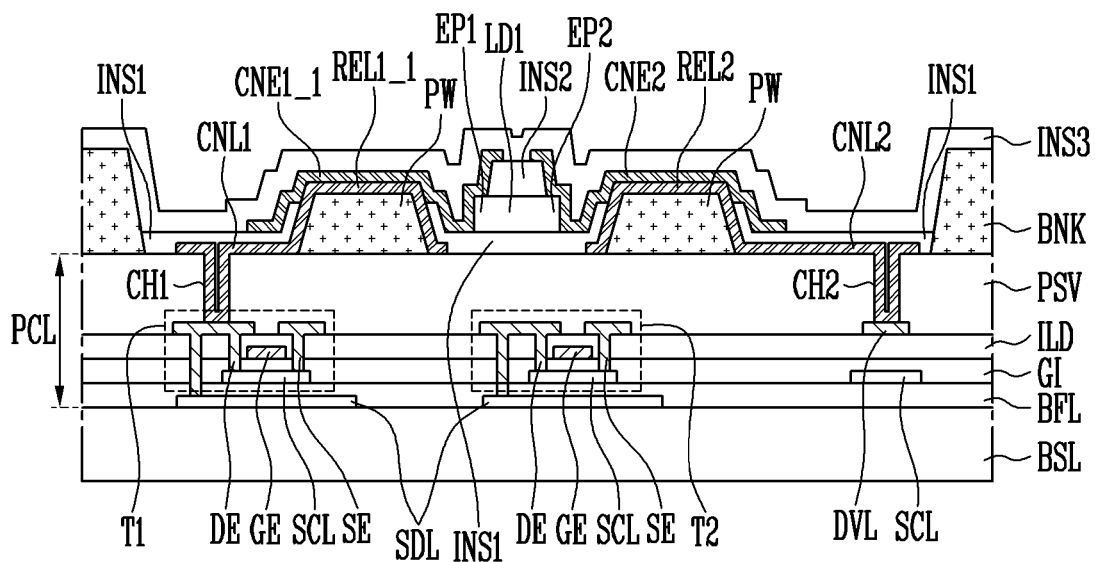

In an embodiment of the present disclosure, the partition wall PW and the bank BNK may be provided on the same surface and formed and/or provided through the same process. The partition wall PW and the bank BNK may be provided integrally with each other and may include the same material. In the case where the partition wall PW provided in the emission area EMA of each of the first to third sub-pixels SP1 to SP3 and the bank BNK provided in the non-emission area PPA of each of the first to third sub-pixels SP1 to SP3 are formed and/or provided through the same process, the number of mask processes may be reduced compared to that of the case where the partition wall PW and the bank BNK are separately formed. Detailed description pertaining to this will be made with reference to FIG. 8B.

The partition wall PW may be spaced by a predetermined distance apart from a partition wall PW disposed adjacent thereto on the passivation layer PSV. Two adjacent partition walls PW may be disposed on the passivation layer PSV and spaced apart from each other by a length L of one light emitting element LD or more. Although the partition wall PW may have a trapezoidal cross-section which is reduced in width upward from one surface of the passivation layer PSV, as illustrated in FIG. 5, the present disclosure is not limited thereto.

In an embodiment, the partition wall PW may include a curved surface having a cross-sectional shape such as a semi-circular shape and a semi-elliptical shape, which is reduced in width upward from the one surface of the passivation layer PSV. In a sectional view, the shape of each of the partition walls PW is not limited to the foregoing examples, and may be changed in various ways within a range in which the efficiency of light emitted from each of the light emitting elements LD can be enhanced. The two adjacent partition walls PW may be disposed on the same plane on the passivation layer PSV and have the same height.

The first connection line CNL1 may extend from each of the first to third sub-pixels SP1 to SP3 in a first direction DR1. The first connection line CNL1 may be provided in only one corresponding sub-pixel so as to independently drive each of the first to third sub-pixels SP1 to SP3.

The second connection line CNL2 may extend in a direction parallel to a direction in which the first connection line CNL1 extends. The second connection line CNL2 may be provided in common to the first to third sub-pixels SP1 to SP3. Therefore, the first to third sub-pixels SP1 to SP3 may be connected in common to the second connection line CNL2.

Each of the first and second electrodes REL1 and REL2 may be provided in the emission area EMA of each of the first to third sub-pixels SP1 to SP3 and extend in a second direction DR2 intersecting with the first direction DR1. The first and second electrodes REL1 and REL2 may be provided on the same plane and spaced apart from each other by a predetermined distance.

The first electrode REL1 may be connected to the first connection line CNL1. For instance, the first electrode REL1 may be integrally connected to the first connection line CNL1. For instance, the first electrode REL1 may include a 1-1-th electrode REL1_1 and a 1-2-th electrode REL1_2 which diverge in the second direction DR2 from the first connection line CNL1 extending in the first direction DR1. The 1-1-th electrode REL1_1, the 1-2-th electrode REL1_2, and the first connection line CNL1 may be integrally provided and electrically and/or physically connected to each other. In the case where the first electrode REL1 and the first connection line CNL1 are formed and/or provided integrally with each other, the first connection line CNL1 may be regarded as one area of the first electrode REL1. However, the present disclosure is not limited thereto. For example, in some embodiments, the first electrode REL1 and the first connection line CNL1 may be individually formed and electrically connected to each other through a contact hole, via hole, or the like, which is not illustrated.

The second electrode REL2 may extend in the second direction DR2 and be electrically connected with the second connection line CNL2. In an embodiment of the present disclosure, the second electrode REL2 may diverge from the second connection line CNL2 in the second direction DR2. Hence, the second electrode REL2 and the second connection line CNL2 may be integrally provided and electrically and/or physically connected to each other. In the case where the second electrode REL2 and the second connection line CNL2 are formed and/or provided integrally with each other, the second connection line CNL2 may be regarded as one area of the second electrode REL2. However, the present disclosure is not limited thereto. For example, in some embodiments, the second electrode REL2 and the second connection line CNL2 may be individually formed and electrically connected to each other through a contact hole, via hole, or the like, which is not illustrated.

Each of the first and second electrodes REL1 and REL2 may function as an alignment electrode for aligning the light emitting elements LD in the emission area EMA of each of the first to third sub-pixels SP1 to SP3.

Before the light emitting elements LD are aligned in the emission area EMA of each of the first to third sub-pixels SP1 to SP3, a first alignment voltage may be applied to the first electrode REL1 through the first connection line CNL1, and a second alignment voltage may be applied to the second electrode REL2 through the second connection line CNL2. The first alignment voltage and the second alignment voltage may have different voltage levels. As predetermined alignment voltages having different voltage levels are respectively applied to the first electrode REL1 and the second electrode REL2, an electric field may be formed between the first electrode REL1 and the second electrode REL2. Hence, the light emitting elements LD may be aligned between the first electrode REL1 and the second electrode REL2.

In a plan view, the second electrode REL2 may be provided between the 1-1-th electrode REL1_1 and the 1-2-th electrode REL1_2 and spaced apart from each of the 1-1-th and 1-2-th electrodes REL1_1 and REL1_2 by a predetermined distance. The 1-1-th electrode REL1_1, the 1-2-th electrode REL1_2, and the second electrode REL2 may be alternately disposed on the passivation layer PSV.

After the light emitting elements LD are aligned in the emission area EMA of each of the first to third sub-pixels SP1 to SP3, each of the first and second electrodes REL1 and REL2 may function as a driving electrode for driving the light emitting elements LD.

The first and second electrodes REL1 and REL2 may be made of material having a predetermined reflectivity to allow light emitted from the opposite ends EP1 and EP2 of each of the light emitting elements LD to travel in a direction (e.g., in a frontal direction) in which an image of the display device is displayed.

In an embodiment of the present disclosure, the first and second electrodes REL1 and REL2, the first connection line CNL1, and the second connection line CNL2 may be provided on the same layer and formed of the same material.

The first and second electrodes REL1 and REL2, the first connection line CNL1, and the second connection line CNL2 may be formed of conductive material having a predetermined reflectivity. The conductive material may include metal such as Ag, Mg, Al, Pt, Pd, Au, Ni, Nd, Ir, Cr, or an alloy of them, a conductive oxide such as an indium tin oxide (ITO), an indium zinc oxide (IZO), a zinc oxide (ZnO), or an indium tin zinc oxide (ITZO), and a conductive polymer such as PEDOT.

The materials of the first and second electrodes REL1 and REL2, the first connection line CNL1, and the second connection line CNL2 are not limited to the foregoing materials.

Each of the first and second electrodes REL1 and REL2, the first connection line CNL1, and the second connection line CNL2 may have a single layer structure, but the present disclosure is not limited thereto, for example, it may have a multi-layer structure formed by stacking two or more materials of metals, alloys, conductive oxides, and conductive polymers.

Each of the first and second electrodes REL1 and REL2, the first connection line CNL1, and the second connection line CNL2 may have a multi-layer structure having at least two or more layers to minimize a voltage drop due to a signal delay when signals are transmitted to the opposite ends EP1 and EP2 of each of the light emitting elements LD.

Since the first and second electrodes REL1 and REL2 have shapes corresponding to the shape of the partition wall PW, light emitted from the opposite ends EP1 and EP2 of each of the light emitting elements LD may be reflected by the first and second electrodes REL1 and REL2 and more effectively travel in the frontal direction of the display device. Consequently, the efficiency of light emitted from the light emitting elements LD may be enhanced.

In an embodiment of the present disclosure, the partition wall PW and the first and second electrodes REL1 and REL2 may function as reflective components enabling light emitted from each of the light emitting elements LD to travel in the frontal direction of the display device, thus enhancing the light output efficiency of the light emitting elements LD.

Any one of the first and second electrodes REL1 and REL2 may be an anode electrode, and the other may be a cathode electrode. In an embodiment of the present disclosure, the first electrode REL1 may be an anode electrode, and the second electrode REL2 may be a cathode electrode.

Each of the light emitting elements LD may be formed of a light emitting diode which is made of material having an inorganic crystal structure and has a subminiature size, e.g., corresponding to a nano-scale or micro-scale size.

Although at least two or tens of light emitting elements LD are provided in the emission area EMA of each of the first to third sub-pixels SP1, SP2, and SP3, the present disclosure is not limited thereto. In an embodiment, the number of light emitting elements LD provided in each sub-pixel may be changed in various ways.

Each of the light emitting elements LD may include a stacked emission pattern formed by successively stacking a first conductive semiconductor layer 11, an active layer 12, a second conductive semiconductor layer 13, and an electrode layer 15 in the longitudinal direction (L) of each light emitting element LD. Furthermore, each of the light emitting elements LD may further include an insulating film 14 which encloses an outer circumferential surface of the stacked emission pattern. In an embodiment of the present disclosure, each of the light emitting elements LD may have a cylindrical shape. In this case, each light emitting element LD may have a first end EP1 corresponding to any one of a lower portion of the cylinder and an upper portion of the cylinder, and a second end EP2 corresponding to the other of the lower portion of the cylinder and the upper portion of the cylinder. Any one of the first conductive semiconductor layer 11 and the electrode layer 15 may be disposed on the first end EP1 of each light emitting element LD, and the other of the first conductive semiconductor layer 11 and the electrode layer 15 may be disposed on the second end EP2 thereof.

In an embodiment of the present disclosure, the light emitting elements LD may be divided into a plurality of first light emitting elements LD1 aligned between the 1-1-th electrode REL1_1 and the second electrode REL2, and a plurality of second light emitting elements LD2 aligned between the second electrode REL2 and the 1-2-th electrode REL1_2.

A second insulating layer INS2 for covering a portion of an upper surface of each of the light emitting elements LD may be provided on the light emitting elements LD. A first insulating layer INS1 may be provided between each of the light emitting elements LD and the passivation layer PSV.

The first insulating layer INS1 may be filled into space between the passivation layer PSV and each of the light emitting elements LD to stably support the light emitting elements LD and prevent the light emitting elements LD from being removed from the passivation layer PSV. The first insulating layer INS1 may be formed of an inorganic insulating layer including inorganic material, or an organic insulating layer including organic material. Although in an embodiment of the present disclosure the first insulating layer INS1 may be formed of an inorganic insulating layer having an advantage in protecting the light emitting elements LD from the pixel circuit layer PCL, the present disclosure is not limited thereto. In an embodiment, the first insulating layer INS1 may be formed of an organic insulating layer that has an advantage in planarization of support surfaces of the light emitting elements LD.

The second insulating layer INS2 may be an organic insulating layer including organic material. In an embodiment of the present disclosure, the second insulating layer INS2 may be provided on a portion of the upper surface of each of the light emitting elements LD such that the opposite ends EP1 and EP2 of each of the light emitting elements LD may be exposed to the outside.

In an embodiment of the present disclosure, the first connection line CNL1 may be electrically connected to the drain electrode DE of the first transistor T1 through the first contact hole CH1 of the passivation layer PSV. Since the first connection line CNL1 is integrally provided with the first electrode REL1, a signal of the first transistor T1 applied to the first connection line CNL1 may be transmitted to the first electrode REL1.

The first electrode REL1 may be disposed adjacent to one end of the opposite ends EP1 and EP2 of each of the light emitting elements LD, and may be electrically connected to each of the light emitting elements LD through the first contact electrode CNE1. Therefore, a signal of the first transistor T1 that is applied to the first electrode REL1 may be transmitted to each of the light emitting elements LD through the first contact electrode CNE1.

In an embodiment of the present disclosure, the second connection line CNL2 may be electrically connected to the driving voltage line DVL through the second contact hole CH2 of the passivation layer PSV. Since the second connection line CNL2 is integrally provided with the second electrode REL2, the voltage of the second driving power supply VSS of the driving voltage line DVL applied to the second connection line CNL2 may be transmitted to the second electrode REL2.

The second electrode REL2 may be disposed adjacent to the other end of the opposite ends EP1 and EP2 of each of the light emitting elements LD, and may be electrically connected to each of the light emitting elements LD through the second contact electrode CNE2. Hence, the voltage of the second driving power VSS applied to the second electrode REL2 may be transmitted to each of the light emitting elements LD.

The first contact electrode CNE1 may be provided on the first electrode REL1 to electrically and/or physically reliably connect the first electrode REL1 with one end of the opposite ends EP1 and EP2 of each of the light emitting elements LD. The first contact electrode CNE1 may be formed of transparent conductive material to allow light emitted from each of the light emitting elements LD and reflected by the first electrode REL1 in the frontal direction of the display device to travel in the frontal direction without loss.

In a plan view, the first contact electrode CNE1 may cover the first electrode REL1 and overlap with the first electrode REL1. Furthermore, the first contact electrode CNE1 may partially overlap with one of the opposite ends EP1 and EP2 of each of the light emitting elements LD. The first contact electrode CNE1 may include a 1-1-th contact electrode CNE1_1 provided on the 1-1-th electrode REL1_1, and a 1-2-th contact electrode CNE1_2 provided on the 1-2-th electrode REL1_2.

The second contact electrode CNE2 may be provided on the second electrode REL2. In a plan view, the second contact electrode CNE2 may cover the second electrode REL2 and overlap with the second electrode REL2. Furthermore, the second contact electrode CNE2 may overlap with the second end EP2 of each of the first light emitting elements LD1 and the first end EP1 of each of the second light emitting elements LD2. The second contact electrode CNE2 may be made of the same material as that of the first contact electrode CNE1, but the present disclosure is not limited thereto.

In an embodiment of the present disclosure, the first contact electrode CNE1 and the second contact electrode CNE2 may be provided on the same plane and spaced apart from each other by a predetermined distance on the second insulating layer INS2 so that the first and second contact electrodes CNE1 and CNE2 can be electrically and/or physically separated from each other. In other words, the first contact electrode CNE1 and the second contact electrode CNE2 may be provided on the same layer and formed through the same manufacturing process.

A third insulating layer INS3 for covering the first and second contact electrodes CNE1 and CNE2 may be provided on the first contact electrode CNE1 and the second contact electrode CNE2. The third insulating layer INS3 may prevent the first and second contact electrodes CNE1 and CNE2 from being exposed to the outside, thus preventing the first and second contact electrodes CNE1 and CNE2 from being corroded.

The third insulating layer INS3 may be formed of an inorganic insulating layer including inorganic material, or an organic insulating layer including organic material. Although the third insulating layer INS3 may have a single layer structure as shown in the drawing, the present disclosure is not limited thereto. For example, the third insulating layer INS3 may have a multi-layer structure. In the case where the third insulating layer INS3 has a multi-layer structure, the third insulating layer INS3 may have a structure formed by alternately stacking a plurality of inorganic insulating layers and a plurality of organic insulating layers. For example, the third insulating layer INS3 may have a structure formed by sequentially stacking a first inorganic insulating layer, an organic insulating layer, and a second inorganic insulating layer.

An overcoat layer (not illustrated) may be provided over the third insulating layer INS3. The overcoat layer may be a planarization layer for mitigating a step difference formed by the partition wall PW, the first and second electrodes REL1 and REL2, the first and second contact electrodes CNE1 and CNE2, etc. that are disposed under the overcoat layer. The overcoat layer may be an encapsulating layer provided to prevent oxygen, water, or the like from penetrating into the light emitting elements LD.

Predetermined voltages may be respectively applied to the opposite ends EP1 and EP2 of each of the light emitting elements LD through the first electrode REL1 and the second electrode REL2. Hence, each of the light emitting elements LD may emit light by coupling of electron-hole pairs in the active layer 12 of each of the light emitting elements LD. Here, the active layer 12 may emit light having a wavelength range from 400 nm to 900 nm.

Figure 6:
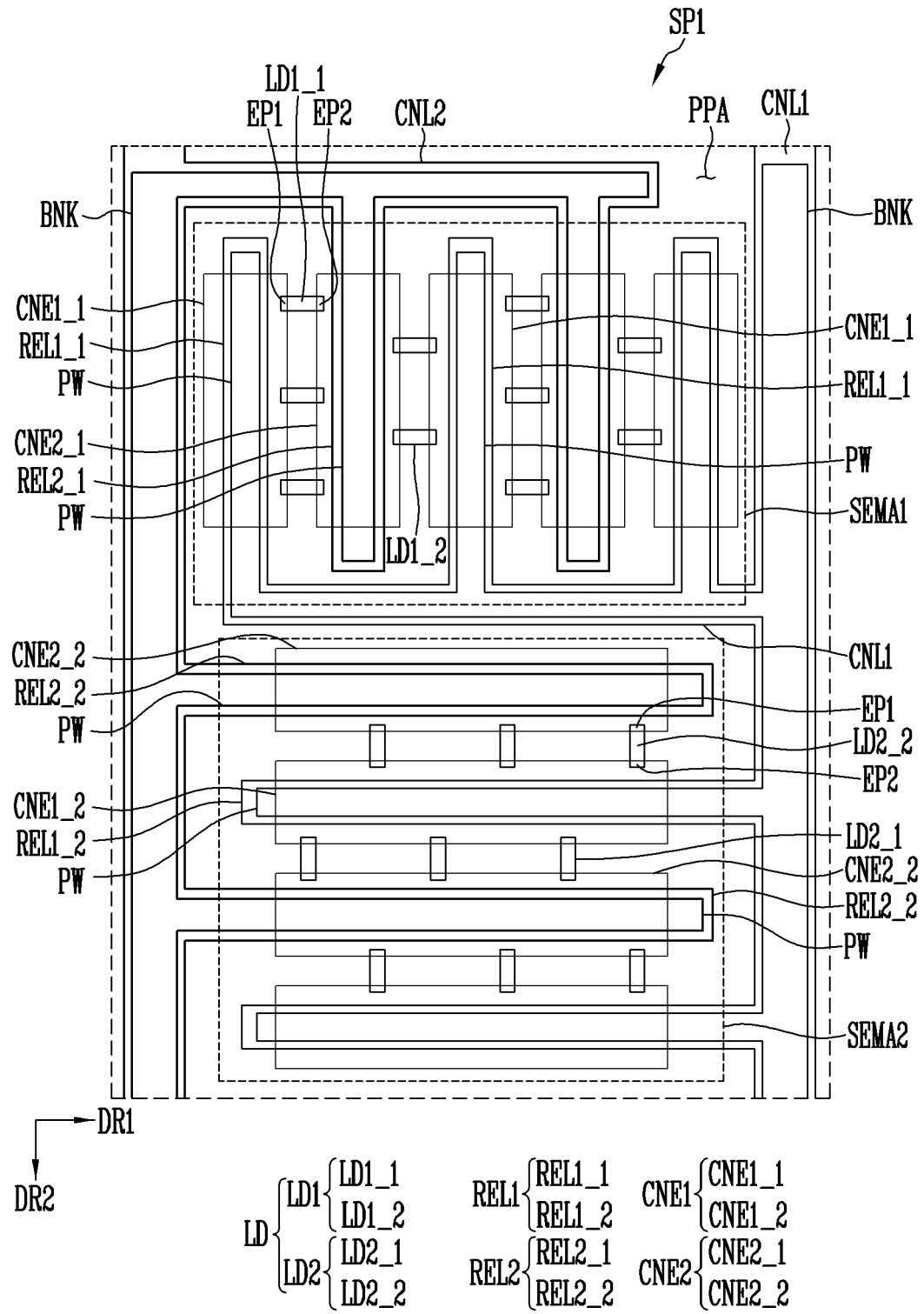
FIG. 6 is a schematic plan view illustrating another embodiment of the first sub-pixel in the pixel of FIG. 4.

FIG. 6 is a schematic plan view illustrating another embodiment of the first sub-pixel in the pixel of FIG. 4.

The configuration of the first sub-pixel illustrated in FIG. 6, other than a structure in which an emission area includes first and second sub-emission areas and alignment shapes of electrodes are different from each other in respective sub-emission areas, may be substantially equal or similar to that of the first sub-pixel of FIG. 4.

Therefore, to avoid redundant explanation, the description of the first sub-pixel of FIG. 6 will be focused on differences from that of the foregoing embodiments. Components which are not separately explained in the following description of the present embodiment comply with that of the foregoing embodiments. The same reference numeral will be used to designate the same component, and a similar reference numeral will be used to designate a similar component.

Referring to FIGS. 1A, 2, 4, and 6, the first sub-pixel SP1 may include an emission area EMA which may emit light, and a non-emission area PPA disposed around the emission area EMA.

A display element layer (refer to DPL of FIG. 5) of the first sub-pixel SP1 may include a partition wall PW, first and second electrodes REL1 and REL2, first and second connection lines CNL1 and CNL2, a plurality of light emitting elements LD, and first and second contact electrodes CNE1 and CNE2 which are provided on a circuit element layer (refer to PCL of FIG. 5).

The light emitting elements LD may include first light emitting elements LD1 and the second light emitting elements LD2. The first light emitting elements LD1 each may include first and second ends EP1 and EP2 with respect to a first direction DR1. Here, the first direction DR1 may refer to a horizontal direction in a plan view. The second light emitting elements LD2 each may include first and second ends EP1 and EP2 with respect to a second direction DR2 intersecting with the first direction DR1. Here, the second direction DR2 may refer to a vertical direction in a plan view. The first light emitting elements LD1 may be aligned in the horizontal direction, and the second light emitting elements LD2 may be aligned in the vertical direction.

In an embodiment of the present disclosure, the emission area EMA of the first sub-pixel SP1 may include a first sub-emission area SEMA1 in which the first light emitting elements LD1 are provided, and a second sub-emission area SEMA2 in which the second light emitting elements LD2 are provided.

In an embodiment of the present disclosure, the first electrode REL1 may include a 1-1-th electrode REL1_1 and a 1-2-th electrode REL1_2, and the second electrode REL2 may include a 2-1-th electrode REL2_1 and a 2-2-th electrode REL2_2.

In a plan view, a portion of the first electrode REL1 and a portion of the second electrode REL2 may be alternately provided in the first direction DR1 in the first sub-emission area SEMA1. For example, the 1-1-th electrode REL1_1 of the first electrode REL1 and the 2-1-th electrode REL2_1 of the second electrode REL2 may be alternately provided in the first direction DR1 in the first sub-emission area SEMA1.

In a plan view, the other portion of the first electrode REL1 and the other portion of the second electrode REL2 may be alternately provided in the second direction DR2 in the second sub-emission area SEMA2. For example, the 1-2-th electrode REL1_2 of the first electrode REL1 and the 2-2-th electrode REL2_2 of the second electrode REL2 may be alternately provided in the second direction DR2 in the second sub-emission area SEMA2.

In an embodiment of the present disclosure, the first contact electrode CNE1 may include a 1-1-th contact electrode CNE1_1 which is provided on the 1-1-th electrode REL1_1 and overlaps with the 1-1-th electrode REL1_1 in a plan view, and a 1-2-th contact electrode CNE1_2 which is provided on the 1-2-th electrode REL1_2 and overlaps with the 1-2-th electrode REL1_2 in a plan view.

Furthermore, the second contact electrode CNE2 may include a 2-1-th contact electrode CNE2_1 which is provided on the 2-1-th electrode REL2_1 and overlaps with the 2-1-th electrode REL2_1 in a plan view, and a 2-2-th contact electrode CNE2_2 which is provided on the 2-2-th electrode REL2_2 and overlaps with the 2-2-th electrode REL2_2 in a plan view.

A distance between the 1-1-th and 2-1-th electrodes REL1_1 and REL2_1 in the first sub-emission area SEMA1 and a distance between the 1-2-th and 2-2-th electrodes REL1_2 and REL2_2 in the second sub-emission area SEMA2, may be designed to be the same as each other. The reason for this is because an alignment surface area of the first light emitting elements LD1 aligned in the first sub-emission area SEMA1 can be formed to be the same as an alignment surface area of the second light emitting elements LD2 aligned in the second sub-emission area SEMA2. In the case where the respective alignment surface areas of the first and second sub-emission areas SEMA1 and SEMA2 are the same as each other, the first and second light emitting elements LD1 and LD2 may be prevented from being biased to one area.

A bank BNK disposed on the same plane as that of the partition wall PW may be provided in the non-emission area PPA of the first sub-pixel SP1. The bank BNK may be formed and/or provided in the non-emission area PPA between the first sub-pixel SP1 and sub-pixels adjacent to the first sub-pixel SP1 to define the emission area EMA of each sub-pixel.

In an embodiment of the present disclosure, the partition wall PW and the bank BNK may be formed of an organic insulating material including organic material, but the present disclosure is not limited thereto. In an embodiment, the partition wall PW and the bank BNK may be formed of an inorganic insulating material including inorganic material, or conductive material which may be prevented from directly affecting the first and second electrodes REL1 and REL2 and the light emitting elements LD due to reflection of external light.

In an embodiment of the present disclosure, for the sake of explanation, there is illustrated an example where the bank BNK provided in the non-emission area PPA of the first sub-pixel SP1 is provided integrally with the partition wall PW provided in each of the first and second sub-emission areas SEMA1 and SEMA2 and thus physically connected with the partition wall PW. However, the present disclosure is not limited to this. In an embodiment, the bank BNK may be provided in the non-emission area PPA of the first sub-pixel SP1, such that the bank BNK is spaced apart from the partition wall PW by a predetermined distance on the same plane.

In the non-emission area PPA of the first sub-pixel SP1, the first and second connection lines CNL1 and CNL2 may be provided on a corresponding bank BNK, and thus overlap with the corresponding bank BNK in a plan view.

Figure 7:
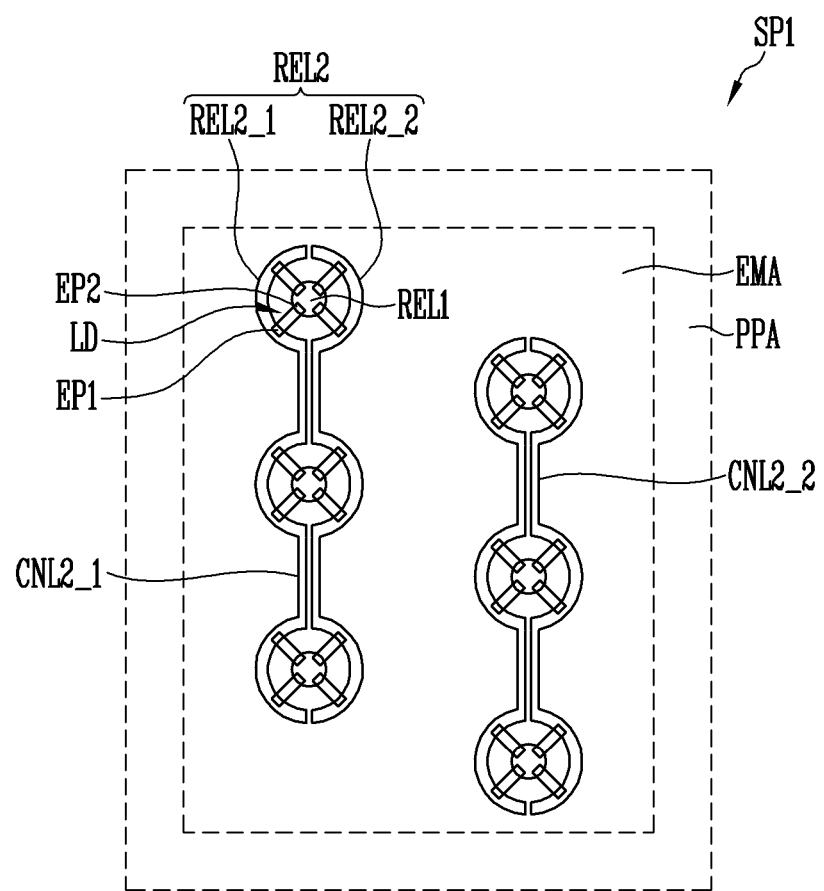
FIG. 7 is a schematic plan view illustrating another embodiment of the first sub-pixel in the pixel of FIG. 4.

FIG. 7 is a schematic plan view illustrating another embodiment of the first sub-pixel in the pixel of FIG. 4.

To avoid redundant explanation, the description of the first sub-pixel of FIG. 7 will be focused on differences from that of the foregoing embodiments. Components which are not separately explained in the following description of the present embodiment comply with that of the foregoing embodiments. The same reference numeral will be used to designate the same component, and a similar reference numeral will be used to designate a similar component.

For the convenience sake of illustration, FIG. 7 illustrates only first and second electrodes, light emitting elements provided between the first and second electrodes, and a second connection line connected to the second electrode.

Referring to FIGS. 1A, 2, 4, and 7, the first sub-pixel SP1 may include an emission area EMA which may emit light, and a non-emission area PPA disposed around the emission area EMA.

A display element layer (refer to DPL of FIG. 5) of the first sub-pixel SP1 may include first and second electrodes REL1 and REL2, a second connection line CNL2, and a plurality of light emitting elements LD which are provided on a circuit element layer (refer to PCL of FIG. 5).

In an embodiment of the present disclosure, the first and second electrodes REL1 and REL2 may be provided on the same plane on the passivation layer PSV and be electrically connected with the light emitting elements LD. Each of the first and second electrodes REL1 and REL2 may have a circular shape. In this case, if the first and second electrodes REL1 and REL2 are respectively supplied with corresponding alignment voltages, an electric field having a radial shape may be formed between the first and second electrodes REL1 and REL2. Hence, the light emitting elements LD may be aligned in various directions along the circumference of the first electrode REL1.

As illustrated in FIG. 1A, each of the light emitting elements LD may have a cylindrical shape. Particularly, each of the light emitting elements LD may include first and second ends EP1 and EP2 in the longitudinal direction (L). The first conductive semiconductor layer 11 may be disposed on any one of the first and second ends EP1 and EP2 of each of the light emitting elements LD. The electrode layer 15 may be disposed on the other of the first and second ends EP1 and EP2 of each of the light emitting elements LD.

Although as shown in the drawings, each of the first and second electrodes REL1 and REL2 may have a circular shape, the present disclosure is not limited thereto, and it may have various shapes such as an elliptical shape, a rectangular shape, and a polygonal shape.

The first electrode REL1 and the second electrode REL2 may be provided in the emission area EMA of the first sub-pixel SP1. The second electrode REL2 may be provided in a shape enclosing the perimeter of the first electrode REL1. Particularly, the second electrode REL2 may extend in a circumferential direction around the first electrode REL1. In an embodiment of the present disclosure, the second electrode REL2 may include a 2-1-th electrode REL2-1 and a 2-2-th electrode REL2_2. The 2-1-th electrode REL2_1 and the 2-2-th electrode REL2_2 may be spaced apart from each other by a predetermined distance.

The 2-1-th electrode REL2_1 may be electrically connected to another 2-1-th electrode REL2_1 disposed on the same column in the second direction DR2 through the 2-1-th connection line CNL2_1. The 2-2-th electrode REL2_2 may be electrically connected to another 2-2-th electrode REL2_2 disposed on the same column in the second direction DR2 through the 2-2-th connection line CNL2_2.

FIGS. 8A to 8H are sectional diagrams sequentially illustrating a method of manufacturing the display device of FIG. 5.

Referring to FIGS. 1A to 8A, the pixel circuit layer PCL is formed on the respective base layers BSL of the first to third sub-pixels SP1, SP2, and SP3. The pixel circuit layer PCL may include the light shielding pattern SDL, the first and second transistors T1 and T2, the driving voltage line DVL, and the passivation layer PSV.

The passivation layer PSV may include the first contact hole CH1 which exposes the drain electrode DE of the first transistor T1, and the second contact hole CH2 which exposes the driving voltage line DVL.

Referring to FIGS. 1A to 8B, after an insulating material layer (not illustrated) is applied to the passivation layer PSV, the partition wall PW is formed in the emission area EMA of each of the first to third sub-pixels SP1, SP2, and SP3 by patterning the insulating material layer using a mask (not illustrated), and simultaneously, the bank BNK is formed in the non-emission area PPA between the first to third sub-pixels SP1, SP2, and SP3. The mask that is used during the above-mentioned manufacturing process may be a half-tone mask.

In an embodiment of the present disclosure, the partition wall PW and the bank BNK may be provided on the same surface and may include the same material. For example, the partition wall PW and the bank BNK each may be an organic insulating layer including organic material.

As described above, in the case where the passivation layer PSV and the partition wall PW are formed through the same process, the number of masks may be reduced compared to that of the case where the passivation layer PSV and the partition wall PW are formed through separate processes. Hence, the process of manufacturing the display device may be further simplified.

Referring to FIGS. 1A to 8C, the first and second electrodes REL1 and REL2 and the first and second connection lines CNL1 and CNL2 that include conductive material having a high reflectivity are formed on the passivation layer PSV of each sub-pixel including the partition wall PW.

Each of the first and second electrodes REL1 and REL2 may be provided and/or formed on a corresponding partition wall PW in the emission area EMA of each sub-pixel. Each of the first and second connection lines CNL1 and CNL2 may be provided and/or formed in the non-emission area PPA of each sub-pixel.

In an embodiment of the present disclosure, the first connection line CNL1 may be electrically connected to the first transistor T1 of the pixel circuit layer PCL through the first contact hole CH1 of the passivation layer PSV. The first connection line CNL1 may be provided integrally with the first electrode REL1 and electrically and/or physically connected to the first electrode REL1. Hence, a signal (or a voltage) applied to the first transistor T1 may be transmitted to the first electrode REL1 through the first connection line CNL1.

The second connection line CNL2 may be electrically connected to the driving voltage line DVL of the pixel circuit layer PCL through the second contact hole CH2 of the passivation layer PSV. The second connection line CNL2 may be provided integrally with the second electrode REL2 and electrically and/or physically connected to the second electrode REL2. Consequently, the voltage of the second driving power VSS of the driving voltage line DVL may be transmitted to the second electrode REL2 through the second connection line CNL2.

Referring to FIGS. 1A to 8D, after an insulating material layer (not illustrated) is deposited on the passivation layer PSV on which the first and second electrodes REL1 and REL2 are formed, the first insulating layer INS1 is formed by patterning the insulating material layer using a mask (not illustrated).

The first insulating layer INS1 may be formed and/or provided in the emission area EMA of each sub-pixel between the first electrode REL1 and the second electrode REL2 and may be formed and/or provided on the first and second connection lines CNL1 and CNL2 in the non-emission area PPA of each sub-pixel.

Referring to FIGS. 1A to 8E, an electric field is formed between the first electrode REL1 and the second electrode REL2 by respectively applying corresponding alignment voltages to the first and second electrodes REL1 and REL2 of each sub-pixel through the first and second connection lines CNL1 and CNL2. In the case where direct current power or alternating current power having predetermined voltage and period is repeatedly applied several times to each of the first and second electrodes REL1 and REL2 through the first and second connection lines CNL1 and CNL2, an electric field may be formed between the first and second electrodes REL1 and REL2 by a difference in potential between the first and second electrodes REL1 and REL2.

After an electric field is formed between the first electrode REL1 and the second electrode REL2 that are formed in the emission area EMA of each sub-pixel, light emitting elements LD are supplied in an inkjet printing scheme or the like. For example, the light emitting elements LD may be supplied onto the passivation layer PSV of the emission area EMA of such sub-pixel by disposing a nozzle over the passivation layer PSV and dropping a solution including the light emitting elements LD onto the passivation layer PSV through the nozzle. The solution may be any one of acetone, water, alcohol, and toluene, but the present disclosure is not limited thereto. For example, the solution may include material which may be vaporized at the room temperature or by heat. Furthermore, the solution may have the form of ink or paste. A method of supplying the light emitting elements LD is not limited to the foregoing method. The method of supplying the light emitting elements LD may be changed. Subsequently, the solution may be removed.

If the light emitting elements LD are supplied onto the passivation layer PSV, self-alignment of the light emitting elements LD may be induced by the electric field formed between the first electrode REL1 and the second electrode REL2. Hence, the light emitting elements LD may be aligned between the first electrode REL1 and the second electrode REL2. In other words, the light emitting elements LD may be intensively aligned in a target area, e.g., the emission area EMA of each sub-pixel.

Referring to FIGS. 1A to 8F, after the alignment of the light emitting elements LD, the second insulating layer INS2 that covers a portion of the upper surface of each light emitting element LD is formed by applying an insulating material layer (not illustrated) onto the passivation layer PSV and patterning the insulating material layer using a mask (not illustrated). Hence, the opposite ends EP1 and EP2 of each of the light emitting elements LD may be exposed to the outside.

Referring to FIGS. 1A to 8G, after a conductive layer (not illustrated) is formed on the second insulating layer INS2 over an entire surface of the passivation layer PSV, the first and second contact electrodes CNE1 and CNE2 are formed by patterning the conductive layer using a mask (not illustrated).

The first contact electrode CNE1 and the second contact electrode CNE2 may be spaced apart from each other by a predetermined distance on the second insulating layer INS2 and thus electrically and/or physically separated from each other.

A portion of the first connection line CNL1 connected and/or provided in common to the sub-pixels may be removed through the foregoing mask process so that each sub-pixel can be driven independently from adjacent sub-pixels. Hence, each sub-pixel may be individually driven, and the display device in accordance with an embodiment of the present disclosure may be implemented as an active matrix-type display device.

Referring to FIGS. 1A to 8H, the third insulating layer INS3 is formed on the first and second contact electrodes CNE1 and CNE2.

In the display device manufactured through the foregoing manufacturing process, during a process of manufacturing the display element layer DPL, the partition wall PW is formed in the emission area EMA of each sub-pixel, and simultaneously, the bank BNK is formed in the non-emission area PPA of each sub-pixel. Hence, the number of mask processes may be reduced.

Figure 9:
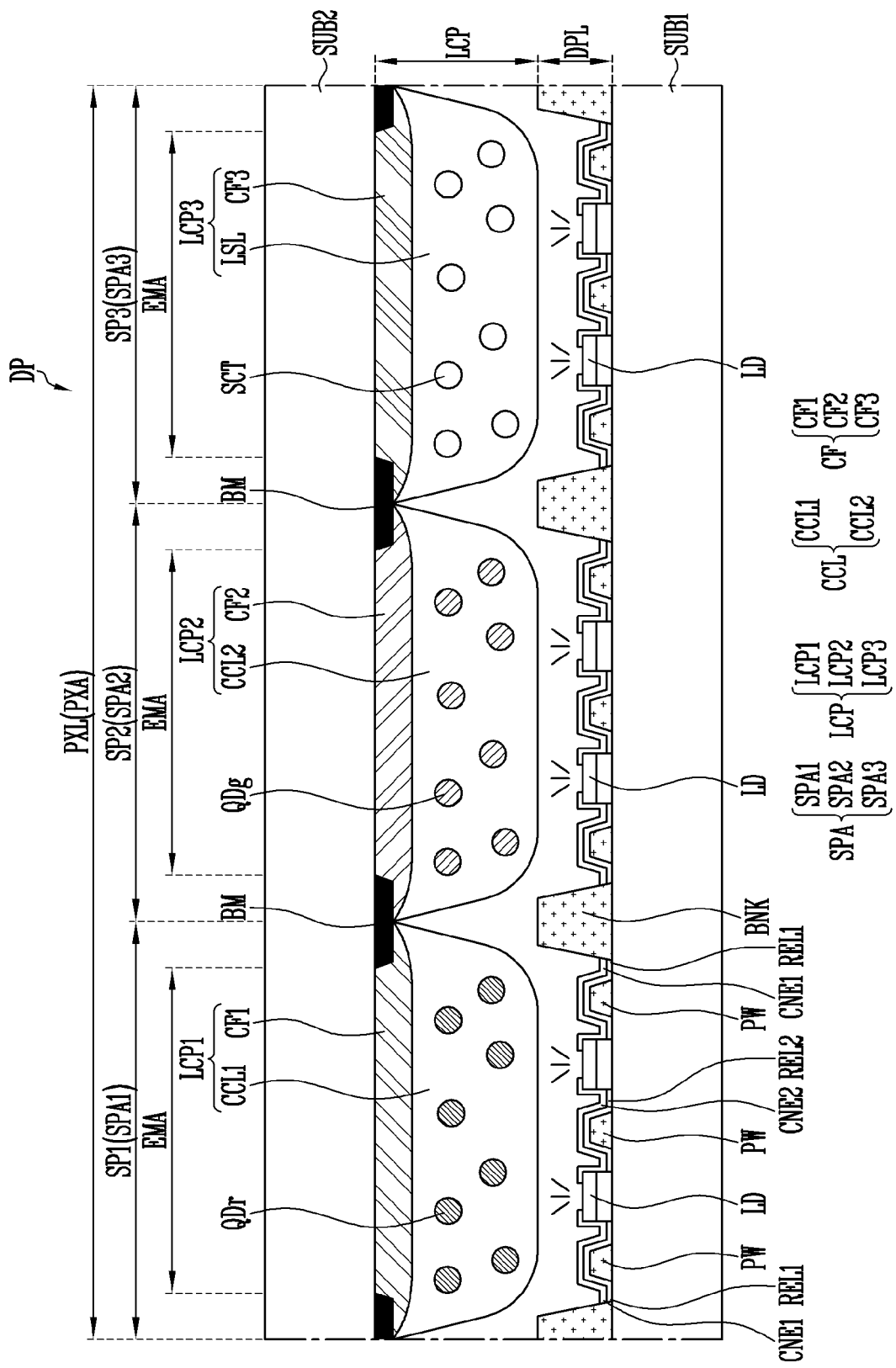
FIG. 9 illustrates a display device in accordance with an embodiment of the present disclosure, and is a schematic sectional view illustrating a structure of coupling a color conversion layer to the display device of FIG. 5.

FIG. 9 illustrates a display device in accordance with an embodiment of the present disclosure, and is a schematic sectional view illustrating a structure of coupling a color conversion layer to the display device of FIG. 5.

FIG. 9 schematically illustrates a pixel area of one pixel of a plurality of pixels included in the display device, for the convenience sake of explanation.

Furthermore, for the convenience sake, in FIG. 9, structures of some components equal to those of the display device that are described in detail with reference to FIG. 5 are schematically illustrated, and detailed explanation thereof will be omitted.

Referring to FIGS. 1A to 9, the display device in accordance with an embodiment of the present disclosure may include a display panel DP that includes a first substrate SUB1 on which at least one pixel PXL (hereinafter, referred to as 'pixel') including first to third sub-pixels SP1, SP2, and SP3 is provided, and a second substrate SUB2 connected with the first substrate SUB1.

In an embodiment of the present disclosure, the pixel PXL is formed and/or provided in the pixel area PXA defined on the first substrate SUB1. The pixel area PXA may include a first sub-pixel area SPA1 in which a first sub-pixel SP1 is formed and/or provided, a second sub-pixel area SPA2 in which a second sub-pixel SP2 is formed and/or provided, and a third sub-pixel area SPA3 in which a third sub-pixel SP3 is formed and/or provided.

In an embodiment of the present disclosure, the first substrate SUB1 may include a base layer BSL, and a pixel circuit layer PCL provided on the base layer BSL. The display element layer DPL may be provided on the first substrate SUB1.

The display element layer DPL may include a partition wall PW, first and second electrodes REL1 and REL2, a plurality of light emitting elements LD, and first and second contact electrodes CNE1 and CNE2 which are provided on the pixel circuit layer PCL of the emission area EMA of each of the first to third sub-pixels SP1, SP2, and SP3. Furthermore, the display element layer DPL may include a bank BNK provided in the non-emission area PPA of each of the first to third sub-pixels SP1, SP2, and SP3.

In an embodiment of the present disclosure, the partition wall PW and the bank BNK may be provided on the same surface and formed through the same process. In an embodiment of the present disclosure, the first and second contact electrodes CNE1 and CNE2 may be provided on the same surface and formed through the same process.

Each of the light emitting elements LD may include opposite ends EP1 and EP2 with respect to the longitudinal direction (L).

The second substrate SUB2 may be disposed over the first substrate SUB1 to cover the display area DA on which the first to third sub-pixels SP1, SP2, and SP3 are disposed. The second substrate SUB2 may form an upper substrate (e.g., an encapsulation substrate or a thin-film encapsulation layer) and/or a window component of the display panel DP. In an embodiment, the second substrate SUB2 may be a rigid substrate or a flexible substrate, and the material or properties thereof are not particularly limited. Furthermore, the second substrate SUB2 may be formed of the same material as that of the first substrate SUB1, or may be formed of material different from that of the first substrate SUB1.

Furthermore, the display panel DP may include a light conversion pattern layer LCP disposed on one surface of the second substrate SUB2 to face the first to third sub-pixels SP1, SP2, and SP3 of the first substrate SUB1.

In an embodiment, the light conversion pattern layer LCP may include a first light conversion pattern layer LCP1 disposed to face the first sub-pixel SP1, a second light conversion pattern layer LCP2 disposed to face the second sub-pixel SP2, and a third light conversion pattern layer LCP3 disposed to face the third sub-pixel SP3. In an embodiment, at least some of the first, second, and third light conversion pattern layers LCP1, LCP2, and LCP3 may include a color conversion layer CCL and/or a color filter CF.

For example, the first light conversion pattern layer LCP1 may include a first color conversion layer CCL1 including first color conversion particles corresponding to a first color, and a first color filter CF1 configured to allow the first color of light to selectively pass therethrough. Likewise, the second light conversion pattern layer LCP2 may include a second color conversion layer CCL2 including second color conversion particles corresponding to a second color, and a second color filter CF2 configured to allow the second color of light to selectively pass therethrough. The third light conversion pattern layer LCP3 may include at least one of a light scattering layer LSL including light scattering particles SCT, and a third color filter CF3 configured to allow the third color of light to selectively pass therethrough.

In an embodiment of the present disclosure, the light emitting elements LD aligned in the emission area EMA of each of the first to third sub-pixels SP1 to SP3 may emit the same color light. A color conversion layer CCL may be disposed on at least some of the first, second, and third sub-pixels SP1, SP2, and SP3. For example, first and second color conversion layers CCL1 and CCL2 may be respectively disposed on the first and second sub-pixels SP1 and SP2. Consequently, the display device in accordance with an embodiment of the present disclosure may display a full-color image.

In an embodiment, the first color conversion layer CCL1 may be disposed on one surface of the second substrate SUB2 to face the first sub-pixel SP1 and may include first color conversion particles which convert the color of light emitted from light emitting elements LD provided on the corresponding sub-pixel to a first color of light. For example, in the case where the first sub-pixel SP1 is a red sub-pixel, the first color conversion layer CCL1 may include red quantum dots QDr, which convert blue light emitted from the light emitting elements LD disposed in the first sub-pixel SP1 to red light.

The first color filter CF1 may be disposed between the first color conversion layer CCL1 and the second substrate SUB2, and may include color filter material which allows the first color of light converted by the first color conversion layer CCL1 to selectively pass therethrough. For example, the first color filter CF1 may be a red color filter.

In an embodiment, the second color conversion layer CCL2 may be disposed on one surface of the second substrate SUB2 to face the second sub-pixel SP2, and may include second color conversion particles which convert the color of light emitted from light emitting elements LD provided on the corresponding sub-pixel to a second color of light. For example, in the case where the light emitting elements disposed in the second sub-pixel SP2 LD are blue light emitting elements configured to emit blue light and the second sub-pixel SP2 are green sub-pixels, the second color conversion layer CCL2 may include green quantum dots QDg which convert blue light emitted from the light emitting elements LD disposed in the second sub-pixel SP2 to green light.

The second color filter CF2 may be disposed between the second color conversion layer CCL2 and the second substrate SUB2, and may include color filter material which allows the second color of light converted by the second color conversion layer CCL2 to selectively pass therethrough. For example, the second color filter CF2 may be a green color filter.

The light scattering layer LSL may be disposed on one surface of the second substrate SUB2 to face the third sub-pixel SP3. For example, the light scattering layer LSL may be disposed between the third sub-pixel SP3 and the third color filter CF3.

The third color filter CF3 may be disposed on one surface of the second substrate SUB2 to face the third sub-pixel SP3, and may include color filter material which allows the color of light emitted from the light emitting elements formed in the corresponding sub-pixel to selectively pass therethrough. For example, the third color filter CF3 may be a blue color filter.

In an embodiment, a black matrix BM may be disposed between the first, second, and third color filters CF1, CF2, and CF3. For example, the black matrix BM may be disposed on the second substrate SUB2 to overlap with the bank BNK on the first substrate SUB1.

As described above, in an embodiment of the present disclosure, each pixel PXL using the light emitting elements LD for emitting the same color light and the display device including the same may be easily manufactured. Since the color conversion layer CCL is disposed on at least some of the sub-pixels, full-color pixels PXL and a display device including the same may be manufactured.

Furthermore, in accordance with an embodiment of the present disclosure, some components of the display element layer DPL may be formed through the same process so that the number of masks can be reduced, whereby the manufacturing process can be simplified.

Figure 10:
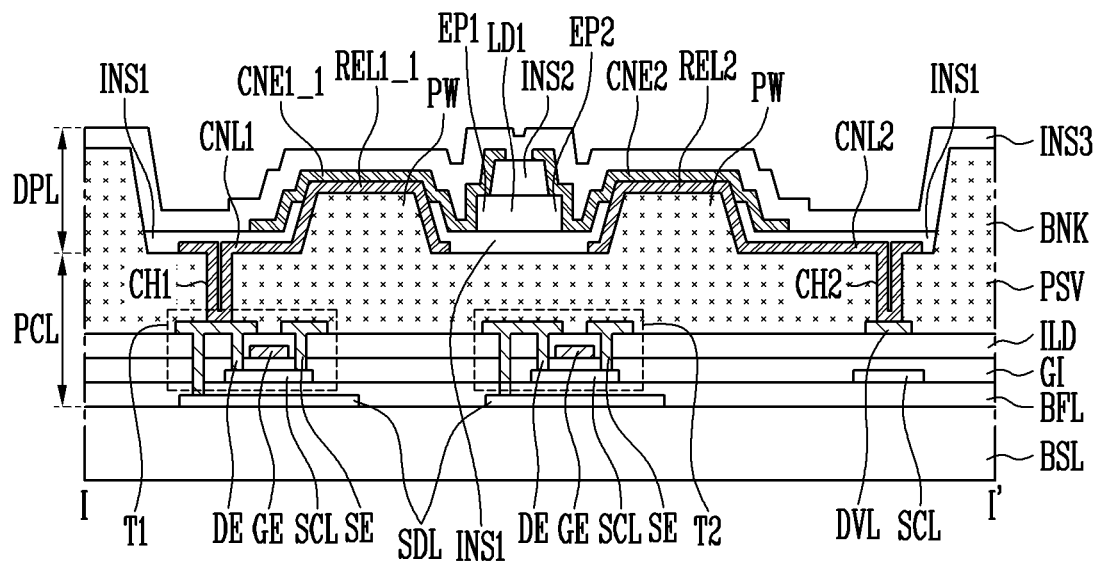
FIG. 10 schematically illustrates a display device in accordance with an embodiment of the present disclosure, and is a sectional diagram corresponding to line I-I' of FIG. 4.
Figure 11A:
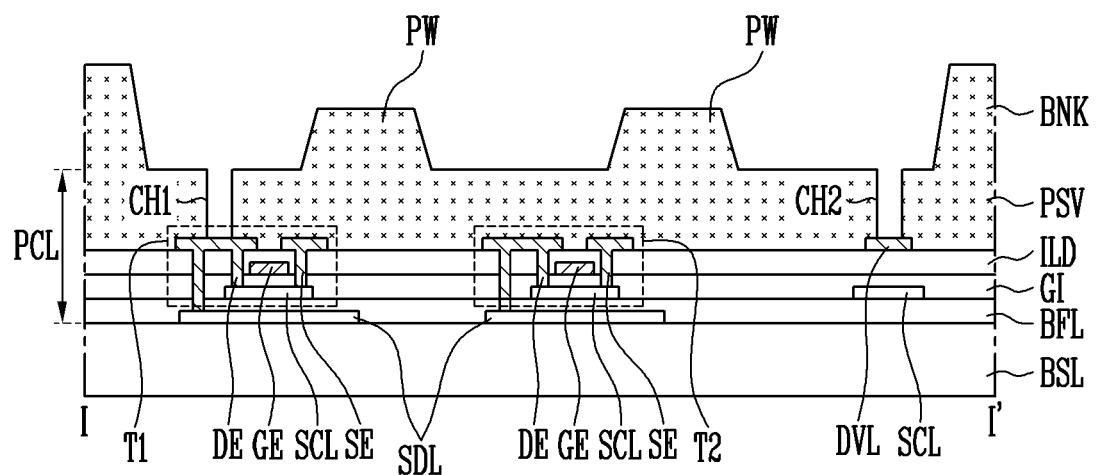
FIGS. 11A to 11G are sectional diagrams sequentially illustrating a method of manufacturing the display device of FIG. 10.
Figure 11B:
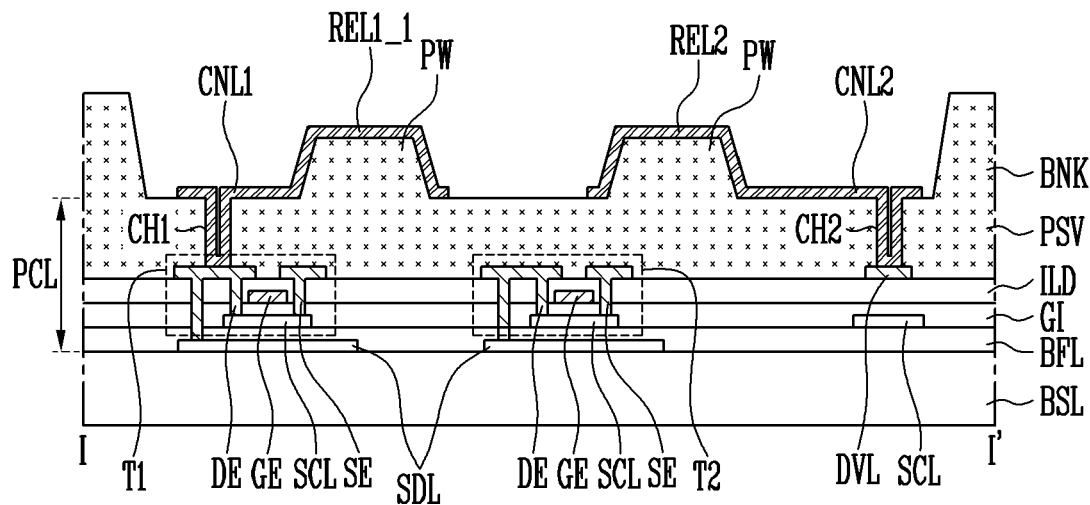
Figure 11C:
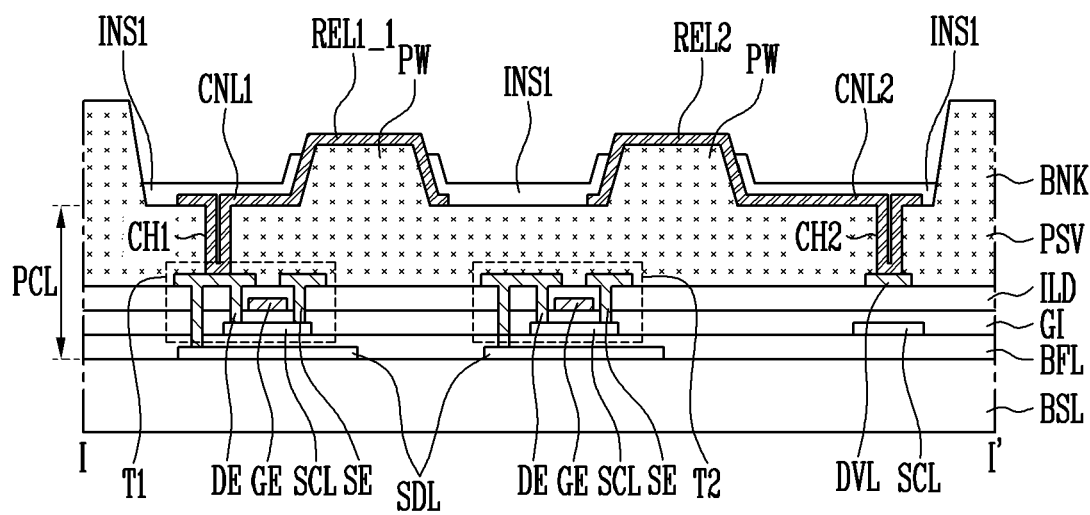
Figure 11D:
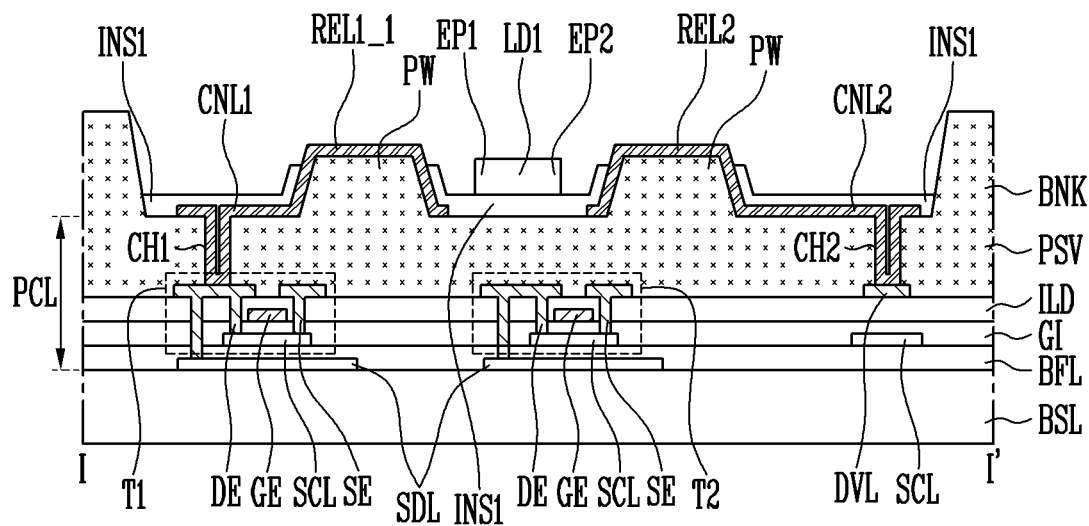
Figure 11E:
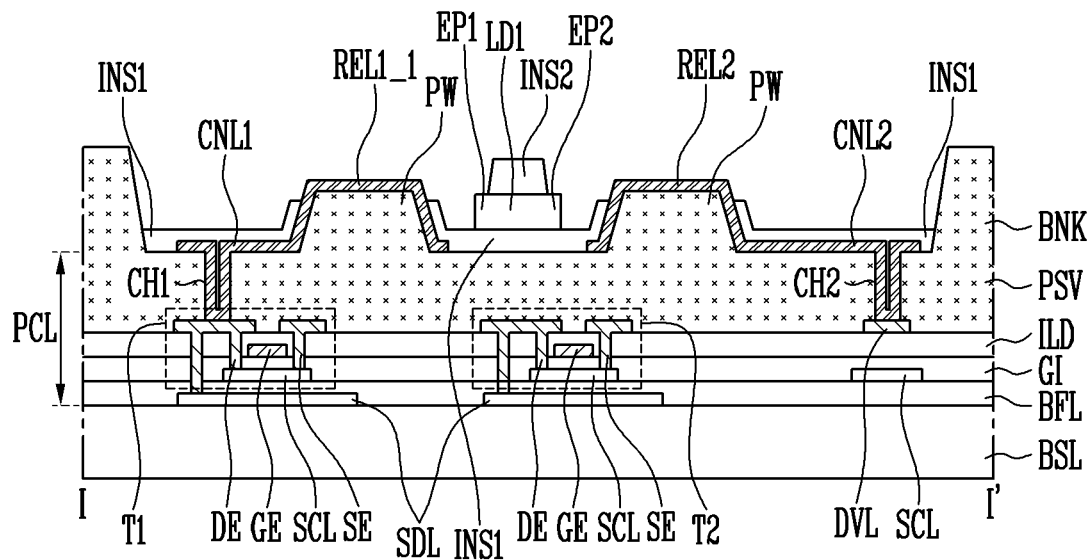
Figure 11F:
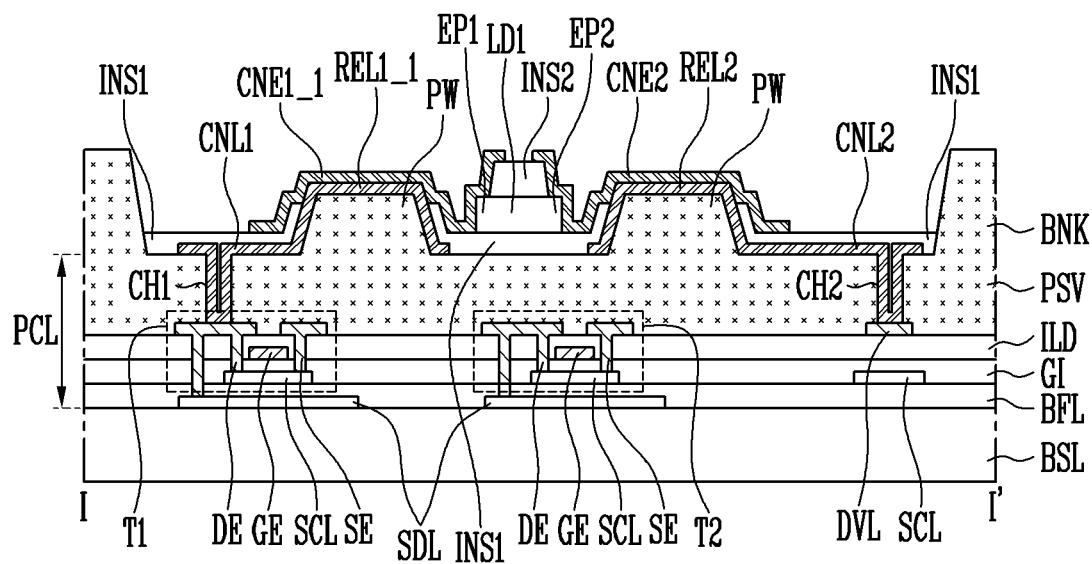
Figure 11G:
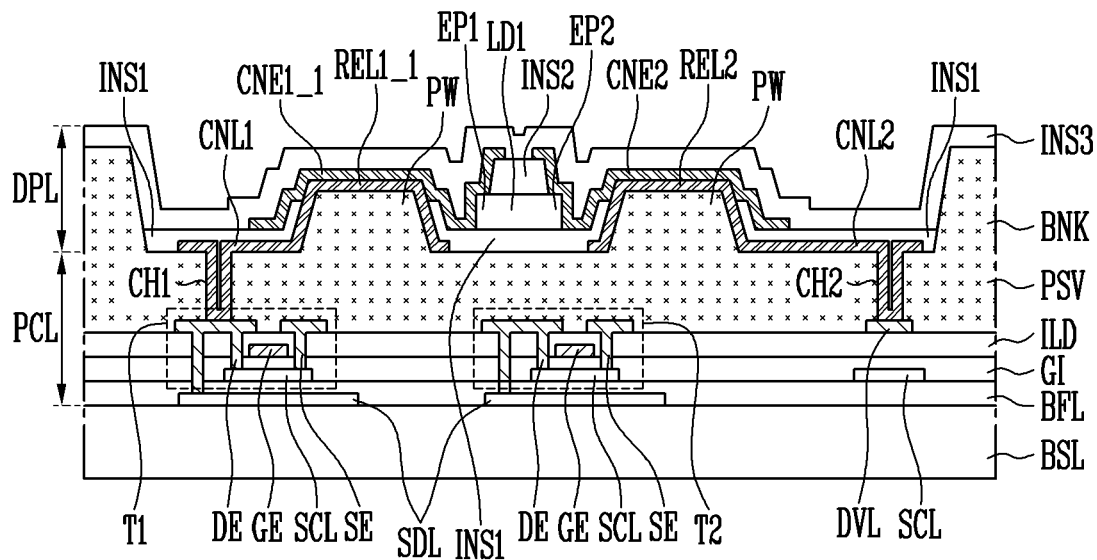

FIG. 10 schematically illustrates a display device in accordance with an embodiment of the present disclosure, and is a sectional diagram corresponding to line I-I' of FIG. 4.

The configuration of the display device of FIG. 10, other than a passivation layer, a partition wall, and a bank that are provided on the same surface and include the same material, may be substantially equal or similar to that of the display device of FIG. 5.

Therefore, to avoid redundant explanation, the description of the display device of FIG. 10 will be focused on differences from the foregoing embodiments. Components which are not separately explained in the following description of the present embodiment comply with that of the foregoing embodiments. The same reference numeral will be used to designate the same component, and a similar reference numeral will be used to designate a similar component.

Referring to FIGS. 1A, 2, 3A, 3B, 3C, 3D, 4, and 10, the display device in accordance with an embodiment of the present disclosure may include a base layer BSL on which a plurality of pixels PXL are provided.

Each of the pixels PXL may include a first sub-pixel SP1, a second sub-pixel SP2, and a third sub-pixel SP3, which are provided on the base layer BSL.

A base layer BSL, a pixel circuit layer PCL, and a display element layer DPL may be provided in the emission area of each of the first to third sub-pixels SP1 to SP3.

The pixel circuit layer PCL may include a light shielding pattern SDL, first and second transistors T1 and T2, a driving voltage line DVL, and a passivation layer PSV, which are provided on the base layer BSL.

The display element layer DPL may include a partition wall PW, a bank BNK, first and second electrodes REL1 and REL2, first and second connection lines CNL1 and CNL2, a plurality of light emitting elements LD, and first and second contact electrodes CNE1 and CNE2.

In an embodiment of the present disclosure, the passivation layer PSV of the pixel circuit layer PCL, and the partition wall PW and the bank BNK of the display element layer DPL may be provided on the same layer and include the same material. In other words, the passivation layer PSV, the partition wall PW, and the bank BNK may be integrally provided through the same process.

The passivation layer PSV, the partition wall PW, and the bank BNK may be formed and/or provided in a target area in each sub-pixel by applying an organic insulating material layer (not illustrated) onto the base layer BSL on which the first and second transistors T1 and T2 are formed, and thereafter patterning the organic insulating material layer using a half-tone mask (not illustrated) or the like. For example, the passivation layer PSV may be formed and/or provided on the first and second transistors T1 and T2 in each sub-pixel. The partition wall PW may be formed and/or provided in the emission area EMA of each sub-pixel. The bank BNK may be formed and/or provided in the non-emission area PPA of each sub-pixel.

FIGS. 11A to 11G are sectional diagrams sequentially illustrating a method of manufacturing the display device of FIG. 10.

Referring to FIGS. 1A, 2, 3A, 3B, 3C, 3D, 4, 10, and 11A, the pixel circuit layer PCL may be provided on the base layer BSL of each of the first to third sub-pixels SP1, SP2, and SP3. The pixel circuit layer PCL may include the light shielding pattern SDL, the first and second transistors T1 and T2, and the driving voltage line DVL.

Thereafter, after an organic insulating material layer (not illustrated) is applied onto the interlayer insulating layer ILD on which the driving voltage line DVL, etc. are formed and/or provided, the organic insulating material layer is patterned by performing a mask process using a half-tone mask (not illustrated). By the foregoing mask process, the partition wall PW is formed in the emission area EMA of each of the first to third sub-pixels SP1 to SP3, and simultaneously, the bank BNK is formed in the non-emission area PPA of each of the first to third sub-pixels SP1 to SP3, and simultaneously, the passivation layer PSV is formed on the driving voltage line DVL.

Furthermore, by the foregoing mask process, the passivation layer PSV may include a first contact hole CH1 which exposes a portion of the drain electrode DE of the first transistor T1 of the pixel circuit layer PCL, and a second contact hole CH2 which exposes a portion of the driving voltage line DVL.

In an embodiment of the present disclosure, the passivation layer PSV, the partition wall PW, and the bank BNK may be integrally provided through the same process. In the case where the passivation layer PSV, the partition wall PW, and the bank BNK are integrally formed and/or provided, the partition wall PW and the bank BNK may be regarded as one area of the passivation layer PSV.

Referring to FIGS. 1A, 2, 3A, 3B, 3C, 3D, 4, 10, 11A, and 11B, the first electrode REL1, the second electrode REL2, and the first and second connection lines CNL1 and CNL2 are formed on the partition wall PW.

The first connection line CNL1 may be electrically connected to the first transistor T1 of the pixel circuit layer PCL through the first contact hole CH1 of the passivation layer PSV. The second connection line CNL2 may be electrically connected to the driving voltage line DVL through the second contact hole CH2 of the passivation layer PSV.

Referring to FIGS. 1A, 2, 3A, 3B, 3C, 3D, 4, 10, and 11A to 11C, the first insulating layer INS1 is formed on the pixel circuit layer PCL on which the first and second electrodes REL1 and REL2, etc. are formed.

Referring to FIGS. 1A, 2, 3A, 3B, 3C, 3D, 4, 10, and 11A to 11D, an electric field is formed between the first electrode REL1 and the second electrode REL2 by respectively applying corresponding alignment voltages to the first and second electrodes REL1 and REL2 of each sub-pixel through the first and second connection lines CNL1 and CNL2.

If the light emitting elements LD are supplied onto the passivation layer PSV, self-alignment of the light emitting elements LD may be induced by the electric field formed between the first electrode REL1 and the second electrode REL2. Hence, the light emitting elements LD may be aligned between the first electrode REL1 and the second electrode REL2. In other words, the light emitting elements LD may be intensively aligned in a target area, e.g., the emission area EMA of each sub-pixel.

Referring to FIGS. 1A, 2, 3A, 3B, 3C, 3D, 4, 10, and 11A to 11E, after the alignment of the light emitting elements LD, the second insulating layer INS2 is formed on a portion of the upper surface of each of the light emitting elements LD. In an embodiment of the present disclosure, the second insulating layer INS2 may be an organic insulating layer including organic material.

Referring to FIGS. 1A, 2, 3A, 3B, 3C, 3D, 4, 10, and 11A to 11F, the first and second contact electrodes CNE1 and CNE2 are formed on the pixel circuit layer PCL on which the second insulating layer INS2 is formed. The first contact electrode CNE1 and the second contact electrode CNE2 may be spaced apart from each other by a predetermined distance on the second insulating layer INS2, and thus be electrically and/or physically separated from each other.

A portion of the first connection line CNL1 connected and/or provided in common to the sub-pixels may be removed through the foregoing mask process so that each sub-pixel can be driven independently from adjacent sub-pixels. Hence, each sub-pixel may be individually driven, and the display device in accordance with an embodiment of the present disclosure may be implemented as an active matrix-type display device.

In an embodiment, when light emitting elements LD are aligned in the emission area EMA of each of the first to third sub-pixels SP1 to SP3, the light emitting elements LD may be aligned between the first and second electrodes REL1 and REL2 using some components included in the pixel circuit layer PCL, rather than applying the alignment voltages to the first and second connection lines CNL1 and CNL2.

For example, as illustrated in FIG. 3D, in the case where the first electrode REL1 (e.g., an anode electrode) is connected to the third transistor T3 in the first sub-pixel SP1 and the second electrode REL2 (e.g., a cathode electrode) is connected to the second driving power supply VSS, the third transistor T3 may be turned on through the control line CLi so that an alignment voltage can be transmitted to the first electrode REL1 through the j-th data line Dj. Here, since the voltage of the second driving power supply VSS is applied to the second electrode REL2, a predetermined electric field may be formed between the first and second electrodes REL1 and REL2. In the case where a solution including light emitting elements LD is dropped onto the first sub-pixel SP1, the light emitting elements LD may be aligned in the emission area EMA of the first sub-pixel SP1 by the electric field formed between the first and second electrodes REL1 and REL2.

In this way, the alignment of the light emitting elements LD in the emission area EMA of the corresponding sub-pixel can be performed using some components of the pixel circuit layer PCL, so that the corresponding sub-pixel can be individually driven. Therefore, a process of forming alignment lines for aligning the light emitting elements LD in the emission area EMA of each sub-pixel, and a process of removing the alignment lines for making it possible to individually drive each sub-pixel, can be omitted.

Consequently, since the process of forming the lines for aligning the light emitting elements LD in the emission area EMA of each sub-pixel and the process of removing the lines can be omitted, the number of mask processes in the display device in accordance with an embodiment of the present disclosure can be further reduced.

Referring to FIGS. 1A, 2, 3A, 3B, 3C, 3D, 4, 10, and 11A to 11G, the third insulating layer INS3 is formed on the first and second contact electrodes CNE1 and CNE2.

In the display device manufactured through the foregoing manufacturing process, during a process of manufacturing the passivation layer PSV, the partition wall PW is formed inthe emission area EMA of each sub-pixel, and simultaneously, the bank BNK is formed in the non-emission area PPA of each sub-pixel. Hence, the number of mask processes may be reduced.

Figure 12:
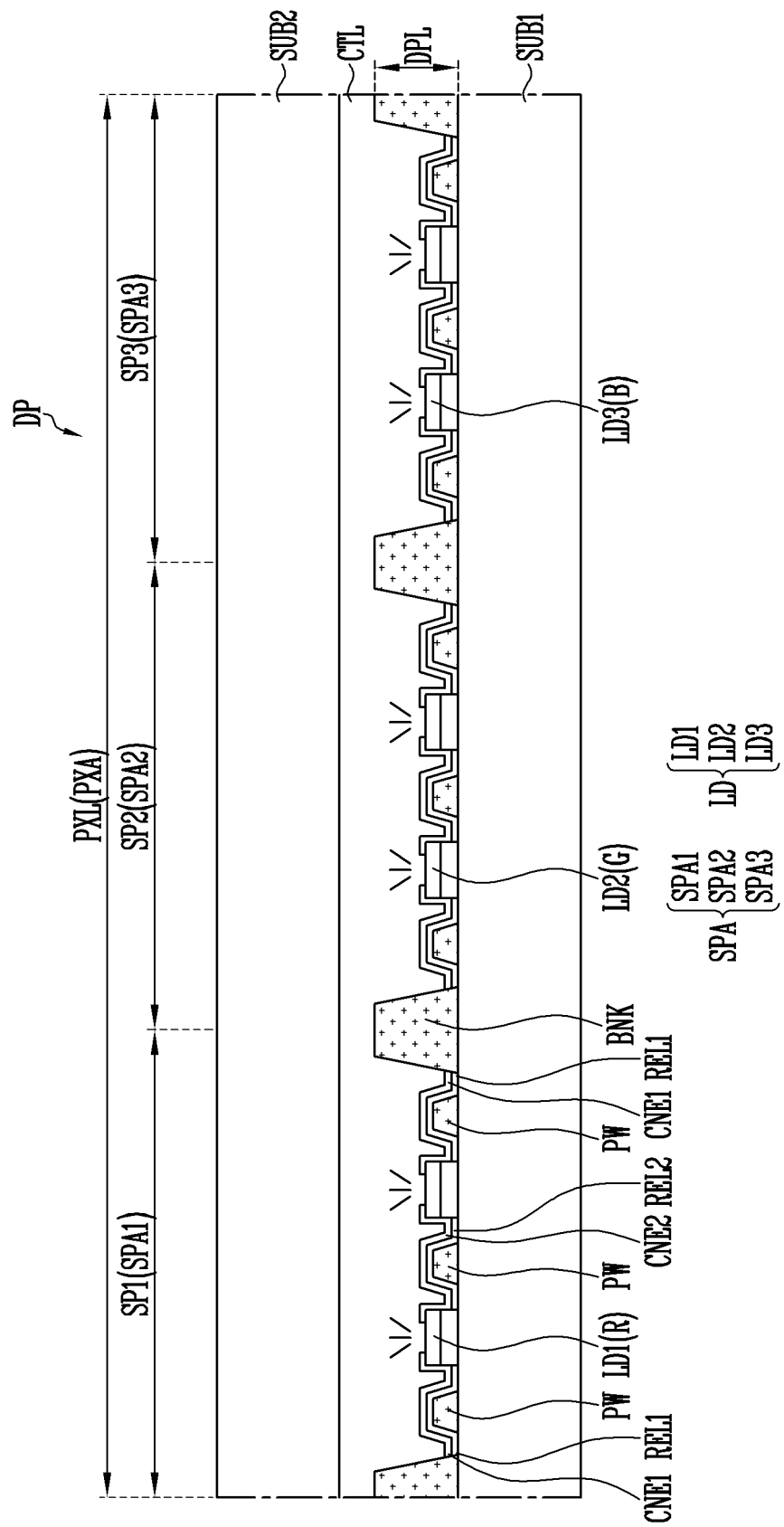
FIG. 12 illustrates a display device in accordance with an embodiment of the present disclosure, and is a schematic sectional view illustrating a structure of coupling a substrate to the display device of FIG. 10.

FIG. 12 illustrates a display device in accordance with an embodiment of the present disclosure, and is a schematic sectional view illustrating a structure of coupling a substrate to the display device of FIG. 10.

FIG. 12 schematically illustrates a pixel area of one pixel of a plurality of pixels included in the display device, for the convenience sake of explanation.

Furthermore, for the convenience sake, in FIG. 12, structures of some components, equal to those of the display device that are described in detail with reference to FIG. 10, are schematically illustrated, and detailed explanation thereof will be omitted.

Referring to FIGS. 1A, 2, 10, and 12 the display device in accordance with an embodiment of the present disclosure may include a display panel DP that includes a first substrate SUB1 on which at least one pixel PXL (hereinafter, referred to as 'pixel') including first to third sub-pixels SP1, SP2, and SP3 is provided, and a second substrate SUB2 connected with the first substrate SUB1.

In an embodiment of the present disclosure, the pixel PXL is formed and/or provided on the pixel area PXA defined on the first substrate SUB1. The pixel area PXA may include a first sub-pixel area SPA1 in which a first sub-pixel SP1 is formed and/or provided, a second sub-pixel area SPA2 in which a second sub-pixel SP2 is formed and/or provided, and a third sub-pixel area SPA3 in which a third sub-pixel SP3 is formed and/or provided.

In an embodiment of the present disclosure, the first substrate SUB1 may include a base layer BSL, and a pixel circuit layer PCL provided on the base layer BSL. The display element layer DPL may be provided on the first substrate SUB1.

The display element layer DPL may include a partition wall PW, first and second electrodes REL1 and REL2, a plurality of light emitting elements LD, and first and second contact electrodes CNE1 and CNE2, which are provided on the pixel circuit layer PCL of the emission area EMA of each of the first to third sub-pixels SP1, SP2, and SP3. Furthermore, the display element layer DPL may include a bank BNK provided in the non-emission area PPA of each of the first to third sub-pixels SP1, SP2, and SP3.

In an embodiment of the present disclosure, the partition wall PW and the bank BNK may be provided on the same surface and formed through the same process. In an embodiment of the present disclosure, the first and second contact electrodes CNE1 and CNE2 may be provided on the same surface and formed through the same process.

Each of the light emitting elements LD may include opposite ends EP1 and EP2 with respect to the longitudinal direction (L). The light emitting elements LD may include a first light emitting element LD1 disposed in the first sub-pixel SP1, a second light emitting element LD2 disposed in the second sub-pixel SP2, and a third light emitting element LD3 disposed in the third sub pixel SP3.

In an embodiment of the present disclosure, the first to third light emitting elements LD1 to LD3 may emit different colors of light. For example, the first light emitting element LD1 may emit red light R, the second light emitting element LD2 may emit green light G, and the third light emitting element LD3 may emit blue light B. Hence, the red light R may be emitted from the first sub-pixel SP1, the green light G may be emitted from the second sub-pixel SP2, and the blue light B may be emitted from the third sub-pixel SP3.

In this case, a light conversion pattern layer (refer to LCP of FIG. 9) configured to convert the color of light emitted from the display element layer DPL to a specific color of light may be omitted.

The second substrate SUB2 may be disposed over the first substrate SUB1 to cover the display area DA in which the first to third sub-pixels SP1, SP2, and SP3 are disposed. The second substrate SUB2 may form an upper substrate (e.g., an encapsulation substrate or a thin-film encapsulation layer) and/or a window component of the display panel DP. In an embodiment, the second substrate SUB2 may be a rigid substrate or a flexible substrate, and the material or properties thereof are not particularly limited. Furthermore, the second substrate SUB2 may be formed of the same material as that of the first substrate SUB1, or may be formed of material different from that of the first substrate SUB1.

In the case where the light conversion pattern layer LCP is omitted, the second substrate SUB2 may be connected to the first substrate SUB1 through an intermediate layer CTL.

The intermediate layer CTL may be provided between the first substrate SUB1 and the second substrate SUB2. The intermediate layer CTL may protect the display element layer DPL between the first substrate SUB1 and the second substrate SUB2, and may function to bond the first substrate SUB1 to the second substrate SUB2. The intermediate layer CTL may have viscosity or adhesion to perform the bonding function. Furthermore, the intermediate layer CTL may be made of transparent material, to allow an image to be transmitted to the second substrate SUB2. In addition, the intermediate layer CTL may be formed of insulating material and have flexibility.

The kind of material of the intermediate layer CTL is not limited so long as the intermediate layer CTL is made of a material which can protect the display element layer DPL on the first substrate SUB1 and function to bond the first substrate SUB1 to the second substrate SUB2. For example, the intermediate layer CTL may be formed of organic material.

While various embodiments have been described above, those skilled in the art will appreciate that various modifications, additions and substitutions are possible, without departing from the scope and spirit of the present disclosure.

Therefore, the embodiments disclosed in this specification are only for illustrative purposes rather than limiting the technical spirit of the present disclosure. The scope of the present disclosure must be defined by the accompanying claims.

The invention claimed is:

1. A display device comprising:
  a base layer comprising a display area and a non-display area; and
  a plurality of pixels in the display area, each pixel of the plurality of pixels comprising a plurality of sub-pixels, wherein each sub-pixel of the plurality of sub-pixels comprises a pixel circuit layer, and a display element layer, the display element layer comprising an emission area to emit light, and a non-emission area around a perimeter of the emission area, wherein the display element layer further comprises:
a partition wall in the emission area of each sub-pixel;
a bank in the non-emission area of each sub-pixel, the bank being on the same surface as the partition wall;
a first electrode and a second electrode on the partition wall and spaced apart from each other; and
at least one light emitting element to emit the light, the at least one light emitting element extending in a longitudinal direction and being between the first and the second electrodes in the emission area of each sub-pixel, wherein the partition wall comprises a partition wall portion extending in an extension direction different from the longitudinal direction such that the partition wall portion is overlapped with an interior of the sub-pixel, wherein the partition wall and the bank are in direct contact with each other, and wherein at least one partition wall is between light emitting elements that are adjacent to each other in the longitudinal direction within each sub-pixel.

2. The display device according to claim 1,
wherein the light-emitting element comprises a first end and a second end opposite the first end, and
wherein the display element layer further comprises:
a first contact electrode to electrically connect the first electrode with one of the first end and the second end of the light emitting element; and
a second contact electrode to electrically connect the second electrode with a remaining one of the first end and the second end of the light emitting element.

3. The display device according to claim 2, wherein the display element layer further comprises:
a first insulating layer between the light emitting element and the pixel circuit layer; and
a second insulating layer on a portion of an upper surface of the light emitting element.

4. The display device according to claim 3, wherein the first contact electrode and the second contact electrode are on an identical layer, and are spaced apart from each other on the second insulating layer and electrically insulated from each other.

5. The display device according to claim 4, wherein the pixel circuit layer comprises:
at least one transistor on the base layer; and
a passivation layer on the at least one transistor.

6. The display device according to claim 5, wherein the passivation layer is on the same surface as the partition wall and the bank.

7. The display device according to claim 6, wherein the passivation layer is integral with the partition wall and the bank, and comprises a material identical with the identical material of the partition wall and the bank.

8. The display device according to claim 7, further comprising a conductive pattern between the base layer and the transistor.

9. The display device according to claim 8, wherein the conductive pattern comprises a light shielding pattern to block light from entering a rear surface of the base layer.

10. The display device according to claim 5, further comprising:

a color conversion layer on the display element layer, the color conversion layer comprising color conversion particles for converting the light to light having a set color; and
a substrate on the color conversion layer.

11. The display device according to claim 5, further comprising:
a substrate on the display element layer; and
an intermediate layer between the display element layer and the substrate.

12. The display device according to claim 11, wherein the intermediate layer comprises an adhesive material for bonding the display element layer to the substrate.

13. The display device according to claim 1, wherein the first electrode and the second electrode are electrically separated from each other, and one of the first and the second electrodes encloses a remaining one of the first electrode or the second electrode.

14. The display device according to claim 1, wherein the light emitting element comprises a subminiature light emitting diode in a shape of a cylinder or a polyprism, the subminiature light emitting diode being of a micro-scale or nano-scale size.

15. The display device according to claim 1, wherein the partition-wall and the bank comprise an identical material and are integral with each other.

16. The display device according to claim 1, wherein the bank and the partition wall are spaced apart from the light emitting elements,
the bank comprises a bank portion extending in the longitudinal direction, and
the partition wall portion is directly connected to a part of the bank portion and extends in the extension direction from the part of the bank portion.

17. The display device according to claim 1, wherein the bank and the partition wall are spaced apart from the light emitting elements,
the bank comprises a first bank portion extending the longitudinal direction and a second bank portion extending the extension direction,
the partition wall portion comprises a first partition wall portion directly connected to the first bank portion and a second partition wall portion spaced apart from the first bank portion, and
the second partition wall portion is disposed between the second bank portion and the first partition wall portion.

18. A method of manufacturing a display device, the method comprising:
providing a base layer comprising a plurality of sub-pixels, each sub-pixel of the plurality of sub-pixels comprising an emission area and a non-emission area; and
forming, on the base layer, a display element layer to emit light from the emission area of each sub-pixel,
wherein the forming the display element layer comprises:
forming a partition wall in the emission area of each sub-pixel, and simultaneously forming a bank in the non-emission area of each sub-pixel, the partition wall and the bank being in direct contact with each other;
forming a first electrode and a second electrode spaced apart from each other on the partition wall;
forming a first insulating layer to expose a portion of an upper surface of each of the first and the second electrodes;
aligning a plurality of light emitting elements between the first and the second electrodes by respectively applying corresponding alignment voltages to the first and the second electrodes, each of the plurality of light emitting elements extending in a longitudinal direction;

forming, on the plurality of light emitting elements, a second insulating layer to expose opposite ends of each of the plurality of light emitting elements; and forming a first contact electrode and a second contact electrode on the second insulating layer, wherein the partition wall comprises a partition wall portion extending in an extension direction different from the longitudinal direction such that the partition wall portion is overlapped with an interior of the sub-pixel, and wherein at least one partition wall is between light emitting elements of the plurality of light emitting elements that are adjacent to each other in the longitudinal direction within each sub-pixel.

19. The method according to claim 18, wherein the first contact electrode and the second contact electrode are on an identical layer, are spaced apart from each other on the second insulating layer, and are electrically insulated from each other.

20. The method according to claim 18, wherein the forming the base layer comprises:
    forming at least one transistor on the base layer; and
    forming a passivation layer on the at least one transistor.

21. The method according to claim 20, wherein the passivation layer is integral with the partition wall and the bank, and the passivation layer, the partition wall, and the bank comprise an identical material.

22. The method according to claim 21, wherein the first electrode and the second electrode are electrically separated from each other, and one of the first and the second electrodes encloses a remaining one of the first electrode or the second electrode.

* * * * *